United States Patent [19]

Eichholtz et al.

[11] Patent Number: 5,866,775

[45] Date of Patent: Feb. 2, 1999

[54] GLYPHOSATE-TOLERANT 5-ENOLPYRUVYL-3-PHOSPHOSHIKIMATE SYNTHASES

[75] Inventors: David Alan Eichholtz, St. Louis, Mo.; Charles Scott Gasser, Davis, Calif.; Ganesh Murthy Kishore, Chesterfield, Mo.

[73] Assignee: Monsanto Company, St. Louis, Mo.

[21] Appl. No.: 590,647

[22] Filed: Sep. 28, 1990

[51] Int. Cl.$^6$ .............. A01H 1/06; A01H 5/00; A01H 5/10; C12N 5/14; C12N 15/29; C12N 15/31; C12N 15/52; C12N 15/82

[52] U.S. Cl. .............. 800/205; 47/58; 47/DIG. 1; 435/172.1; 435/172.3; 435/320.1; 435/419; 536/23.2; 536/23.6; 536/23.7; 800/205; 800/250; 800/255; 800/DIG. 9; 800/DIG. 14; 800/DIG. 17; 800/DIG. 24; 800/DIG. 26; 800/DIG. 27; 800/DIG. 43; 800/DIG. 44; 800/DIG. 57; 800/DIG. 58; 800/DIG. 63

[58] Field of Search .............. 800/205, 250, 800/255, DIG. 9, DIG. 14, DIG. 17, DIG. 24, DIG. 26, DIG. 27, DIG. 43, DIG. 44, DIG. 57, DIG. 58, DIG. 63; 536/27, 23.2, 23.6, 23.7; 435/320.1, 172.1, 172.3, 240.4, 419; 935/35, 64, 67; 47/58

[56] References Cited

U.S. PATENT DOCUMENTS 4,769,061  9/1988  Comai ........................... 71/86
4,971,908  11/1990  Kirshore et al. ............. 435/172.1

FOREIGN PATENT DOCUMENTS 0193259  9/1986  European Pat. Off. ......... 800/205

OTHER PUBLICATIONS

Fitzgibbon (Dec. 1988) Ph.D. thesis, University Microfilms International, 1989, pp. viii–ix, 18, 22–29, 32, 93, and 96–108.
Potrykus (Jun. 1990) Bio/Technology 8:535–542.
Fillatti et al (Jul. 1987) Bio/Technology 5:726–730.
Botterman et al (Aug. 1988) Trends in Genetics 4(8):219–222.
DasSarma et al (Jun. 6, 1986) Science 232:1242–1244.

Primary Examiner—Douglas W. Robinson
Assistant Examiner—Amy J. Nelson
Attorney, Agent, or Firm—Thomas P. McBride; Dennis R. Hoerner, Jr.; Richard H. Shear

[57] ABSTRACT

Glyphosate-tolerant 5-enolpyruvyl-3-phosphoshikimate (EPSP) synthases, DNA encoding glyphsate-tolerant EPSP synthases, plant genes encoding the glyphosate-tolerant enzymes, plant transformation vectors containing the genes, transformed plant cells and differentiated transformed plants containing the plant genes are disclosed. The glyphosate-tolerant EPSP synthases are prepared by substituting an alanine residue for a glycine residue in a first conserved sequence found between positions 80 and 120, and a threonine residue for an alanine residue in a second conserved sequence found between positions 170 and 210 in the mature wild type EPSP synthase.

53 Claims, 6 Drawing Sheets

```
                    1                                                           50
       Petunia.     KPS...EIVL  QPIKEISGTV  KLLGSKSLSN  RILLLAALSE  GTTVVDNLLS
        Tomato.     KPH...EIVL  xPIKDISGTV  KLPGSKSLSN  RILLLAALSE  GRTVVDNLLS
    Arabidopsis.    KAS...EIVL  QPIREISGLI  KLPGSKSLSN  RILLLAALSE  GTTVVDNLLN
       Soybean.     KPSTSPEIVL  EPIKDFSGTI  TLPGSKSLSN  RILLLAALSE  GTTVVDNLLY
         Maize.     ..AGAEEIVL  QPIKEISGTV  KLPGSKSLSN  RILLLAALSE  GTTVVDNLLN
       B.napus      KAS...EIVL  QPIREISGLI  KLPGSxxxxx  RILLLAALSE  GTTVVDNLLN
        E.coli      MES....LTL  QPIARVDGTI  NLPGSKTVSN  RALLLAALAH  GKTVLTNLLD
     Salmonella.    MES....LTL  QPIARVDGAI  NLPGSKSVSN  RALLLAALAC  GKTALTNLLD
      Consensus     ---------L  -------G--  -LPGSK--SN  R-LLLAAL--  G-T----LL- 51                                                         100
       Petunia.     SDDIHYMLGA  LKTLGLHVEE  DSANQRAVVE  GCGGLFPVGK  ESKEEIQLFL
        Tomato.     SDDIHYMLGA  LKTLGLHVED  DNENQRAIVE  GCGGQFPVGK  KSEEEIQLFL
    Arabidopsis.    SDDINYMLDA  LKRLGLNVET  DSENNRAVVE  GCGGIFPASI  DSKSDIELYL
       Soybean.     SEDIHYMLGA  LRTLGLRVED  DKTTKQAIVE  GCGGLFPTSK  ESKDEINLFL
         Maize.     SEDVHYMLGA  LRTLGLSVEA  DKAAKRAVVV  GCGGKFPVE.  DAKEEVQLFL
       B.napus      SDDINYMLDA  LKKLGLNVER  DSVNNRAVVE  GCGGIFPASL  DSKSDIELYL
        E.coli      SDDVRHMLNA  LTALGVSYTL  SADRTRCEII  G....NGGPL  HAEGALELFL
     Salmonella.    SDDVRHMLNA  LSALGINYTL  SADRTRCDIT  G....NGGAL  RAPGALELFL
      Consensus     S-D---ML-A  L--LG-----  ----------  G---------  -------L-L 101                                                        150
       Petunia.     GNAGTAMRPL  TAAVTVAGGN  SRYVLDGVPR  MRERPISDLV  DGLKQLGAEV
        Tomato.     GNAGTAMRPL  TAAVTVAGGH  SRYVLDGVPR  MRERPIGDLV  DGLKQLGAEV
    Arabidopsis.    GNAGTAMRPL  TAAVTAAGGN  ARYVLDGVPR  MRERPIGDLV  VGLKQLGADV
       Soybean.     GNAGTAMRPL  TAAVVAAGGN  ASYVLDGVPR  MRERPIGDLV  AGLKQLGADV
         Maize.     GNAGTAMRPL  TAAVTAAGGN  ATYVLDGVPR  MRERPIGDLV  VGLKQLGADV
       B.napus      GNAGTAMRPL  TAAVTAAGGN  ARYVLDGVPR  MRERPIGDLV  VGLKQLGADV
        E.coli      GNAGTAMRPL  AAALCLGSND  IV..LTGEPR  MKERPIGHLV  DALRLGGAKI
     Salmonella.    GNAGTAMRPL  AAALCLGQNE  IV..LTGEPA  MLERPIGHLV  DSLRQGGANI
      Consensus     GNAGTA-RPL  -AA-------  ----L-G-P-  M-ERPI--LV  --L---GA--

151                                                        200
       Petunia.     DCFLGTKCPP  VRIVSKGGLP  GGKVKLSGSI  SSQYLTALLM  AAPL....AL
        Tomato.     DCSLGTNCPP  VRIVSKGGLP  GGKVKLSGSI  SSQYLTALLM  AAPL....AL
    Arabidopsis.    ECTLGTNCPP  VRVNANGGLP  GGKVKLSGSI  SSQYLTALLM  SAPL....AL
       Soybean.     DCFLGTNCPP  VRVNGKGGLP  GGKVKLSGSV  SSQYLTALLM  AAPL....AL
         Maize.     DCFLGTDCPP  VRVNGIGGLP  GGKVKLSGSI  SSQYLSALLM  AAPL....AL
       B.napus      ECTLGTNCPP  VRVNANGGLP  GGKVKLSGSI  SSQYLTALLM  AAPL....AL
        E.coli      TYLEQENYPP  LRLQGGF..T  GGNVDVGSV   SSQFLTALLM  TAPL....AP
     Salmonella.    DYLEQENYPP  LRLRGGF..T  GGDIEVDGSV  SSQFLTALLM  TAPL....AP
      Consensus     --------PP  -R--------  -G-----GS-  SSQ-L-ALLM  -AP-------

201                                                        250
       Petunia.     GDVEIEIIDK  LISVPYVEMT  LKLMERFGIS  VEHSSSWDRF  FVRGGQKYKS
        Tomato.     GDVEIEIIDK  LISVPYVEMT  LKLMERFGVF  VEHSSGWDRF  LVKGGQKYKS
    Arabidopsis.    GDVEIEIVDK  LISVPYVEMT  LKLMERFGVS  VEHSDSWDRF  FVKGGQKYKS
       Soybean.     GDVEIEIVDK  LISVPYVEMT  LKLMERFGVS  VEHSGNWDRF  LVHGGQKYKS
         Maize.     GDVEIEIIDK  LISIPYVEMT  LRLMERFGVK  AEHSDSWDRF  YIKGGQKYKS
       B.napus      GDVEIEIIDK  LISVPYVEMT  LKLMERFGVS  AEHSDSWDRF  FVKGGQKYKS
        E.coli      EDTVIRIKGD  LVSKPYIDIT  LNLMKTFGVE  IENQHYQQ.F  VVKGGQSYQS
     Salmonella.    KDTIIRVKGE  LVSKPYIDIT  LNLMKTFGVE  IANHHYQQ.F  VVKGGQQYHS
      Consensus     -D--I-----  L-S-PY---T  L-LM--FGV-  ----------F  -------Y--
```

Fig. 1a page 1 of 2

```
                  251                                                              300
   Petunia.   PRKAFVEGDA SSASYFLAGA AVTGGTITVE GCGTNSLQGD VKFAEVLEKM
    Tomato.   PGKAFVEGDA SSASYFLAGA AVTGGTVTVE GCGTSSLQGD VKFAEVLEKM
Arabidopsis.  PGNAYVEGDA SSACYFLAGA AITGETVTVE GCGTTSLQGD VKFAEVLEKM
   Soybean.   PGNAFVEGDA SSASYLLAGA AITGGTITVN GCGTSSLQGD VKFAEVLEKM
     Maize.   PKNAYVEGDA SSATYFLAGA AITGGTVTVE GCGTTSLQGD VKFAEVLEMM
   B.napus    PGNAYVEGDA SSASYFLAGA AITGETVTVE GCGTTSLQxx xxxxxxxxxx
     E.coli   PGTYLVEGDA SSASYFLAAA AIKGGTVKVT GIGRNSMQGD IRFADVLEKM
 Salmonella.  PGRYLVEGDA SSASYFLAAG AIKGGTVKVT GIGRKSMQGD IRFADVLELM
 Consensus    P----VEGDA S-A-Y-LA-- A--G----V- G-G--S-QGD --FA--L--M 301                                                              350
   Petunia.   GAEVTWTENS VTVKGPPRSS SGRKHLRAID VNMNKMPDVA MTLAVVALYA
    Tomato.   GAEVTWTENS VTVKGPPRNS SGMKHLRAID VNMNKMPDVA MTLAVVALFA
Arabidopsis.  GCKVSWTENS VTVTGPPRDA FGMRHLRAID VNMNKMPDVA MTLAVVALFA
   Soybean.   GAKVTWSENS VTVSGPPRDF SGRKVLRGID VNMNKMPDVA MTLAVVALFA
     Maize.   GAKVTWTETS VTVTGPPRSH FGRKHLKAID VNMNKMPDVA MTLAVVALFA
   B.napus    xxxxxxxxxx xxxxxxxxxx xxxxxxxxxx xxxxxxxxxx xxxxxxxxxx
     E.coli   GATICWGDDY I........S CTRGELNAID MDMNHIPDAA MTIATAALFA
 Salmonella.  GATITWGDDF I........A CTRGELHAID MDMNHIPDAA MTIATTALFA
 Consensus    G--------- ---------- -----L---D ------PD-A MT-A--AL-A 351                                                              400
   Petunia.   DGPTAIRDVA SWRVKETERM IAICTELRKL GATVEEGPDY CIITPPEKLN
    Tomato.   DGPTTIRDVA SWRVKETERM IAICTELRKL GATVVEGSDY CIITPPEKLN
Arabidopsis.  DGPTTIRDVA SWRVKETERM IAICTELRKL GATVEEGSDY CVITPPKK..
   Soybean.   NGPTAIRDVA SWRVKETERM IAICTELRKL GATVEEGPDY CVITPPEKLN
     Maize.   DGPTAIRDVA SWRVKETERM VAIRTELTKL GASVEEGPDY CIITPPEKLN
   B.napus    xxxxxxxxxx xxxxKETERM IAICTELRKL GATVEEGSDY CVITPPAK..
     E.coli   KGTTRLRNIY NWRVKETDRL FAMATELRKV GAEVEEGHDY IRITPPEKLN
 Salmonella.  KGTTTLRNIY NWRVKETDRL FAMATELRKV GAEVEEGHDY IRITPPAKLQ
 Consensus    -G----R--- -WRVKET-R- -A--TEL-K- GA-V--G-D- ----PP----

401                                                              450
   Petunia.   V..TDIDTYD DHRMAMAFSL AACADVPVTI NDPSCTRKTF PNYFDVLQQY
    Tomato.   V..TEIDTYD DHRMAMAFSL AACADVPVTI KNPGCTRKTF PDYFEVLQKY
Arabidopsis.  VKTAEIDTYD DHRMAMAFSL AACADVPITI NDSGCTRKTF PDYFQVLERI
   Soybean.   V..TAIDTYD DHRMAMAFSL AACGDVPVTI KDP.CTRKTF PDYFEVLERL
     Maize.   V..TAIDTYD DHRMAMAFSL AACAEVPVTI RDPGCTRKTF PDYFDVLSTF
   B.napus    VKPAEIDTYD DHRMAMAFSL AACADVPVTI KDxxxxxxxx xxxxxxxxxx
     E.coli   F..AEIATYN DHRMAMCFSL VALSDTPVTI LDPKCTAKTF PDYFEQLARI
 Salmonella.  ..HADIGTYN DHRMAMCFSL VALSDTPVTI LDPKCTAKTF PDYFEQLARM
 Consensus    ------I-T-- DHRMAM-F-L -A-----V-I ----C--KTF P-YF------

451
   Petunia.   SKH.
    Tomato.   SKH.
Arabidopsis.  TKH.
   Soybean.   TKH.
     Maize.   VKN.
   B.napus    xxx.
     E.coli   SQAA
 Salmonella.  STPA
 Consensus    -----
```

Fig. 1b      page 2 of 2

GLYPHOSATE-TOLERANT 5-ENOLPYRUVYL-3-PHOSPHOSHIKIMATE SYNTHASES

BACKGROUND OF THE INVENTION

Recent advances in genetic engineering have provided the requisite tools to transform plants to contain foreign genes. It is now possible to produce plants which have unique characteristics of agronomic importance. Certainly, one such advantageous trait is herbicide tolerance. Herbicide-tolerant crop plants could reduce the need for tillage to control weeds, thereby effectively reducing costs to the farmer.

One herbicide which is the subject of much investigation in this regard is N-phosphonomethylglycine.

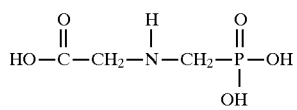

This herbicide is a non-selective, broad spectrum, postemergence herbicide which is registered for use on more than fifty crops. This molecule is an acid, which dissociates in aqueous solution to form phytotoxic anions. Several anionic forms are known. As used herein, the term "glyphosate" refers to the acid and its anions.

Glyphosate inhibits the shikimic acid pathway which provides a precursor for the synthesis of aromatic amino acids. Specifically, glyphosate inhibits the conversion of phosphoenolpyruvate and 3-phosphoshikimic acid to 5-enolpyruvyl-3-phosphoshikimic acid by inhibiting the enzyme 5-enolpyruvyl-3-phosphoshikimate synthase (EPSPS or EPSP synthase).

It has been shown that glyphosate-tolerant plants can be produced by inserting into the genome of the plant the capacity to produce a higher level of EPSP synthase.

The present invention provides a means of enhancing the effectiveness of glyphosate-tolerant plants by producing variant EPSP synthase enzymes which exhibit a lower affinity for glyphosate while maintaining catalytic activity.

BRIEF DESCRIPTION OF THE DRAWINGS

FIGS. 1A–1B show the amino acid sequences for EPSP synthase enzymes from various plant and bacterial species.

STATEMENT OF THE INVENTION

Figure 2:
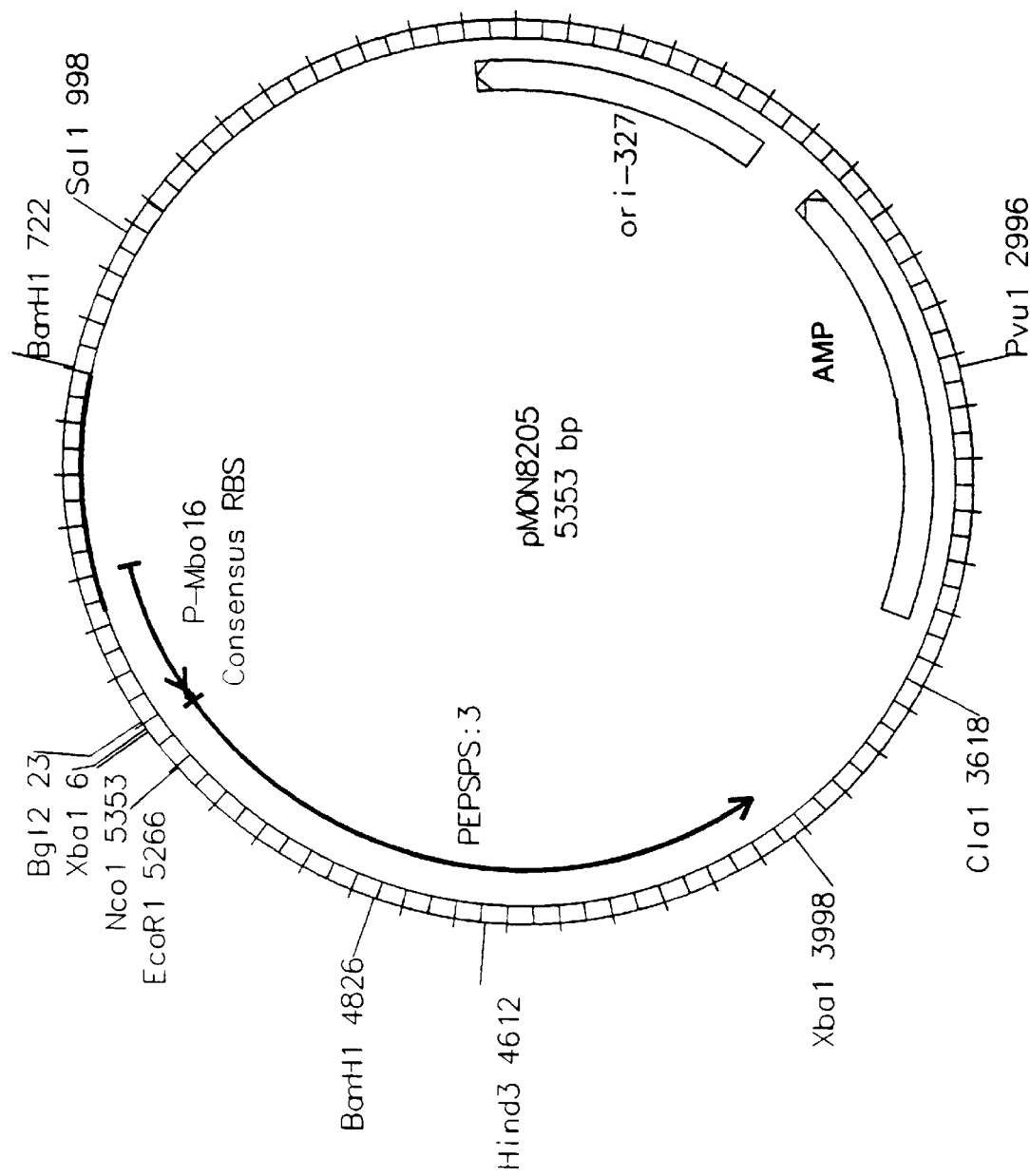
FIG. 2 represents a map of plasmid pMON8205.

The present invention provides a novel EPSP synthase enzyme which exhibits increased tolerance to glyphosate herbicide while also exhibiting lower $K_m$ values for phosphoenolpyruvate than other variant EPSP synthase enzymes. The subject enzyme of this invention has an alanine for glycine substitution and a threonine for alanine substitution as described hereinafter.

In another aspect, the present invention provides a method for the isolation of amino acid substitutions in EPSP synthase which will maintain a high level of glyphosate tolerance while lowering the $K_m$ values for phosphoenolpyruvate.

All peptide structures represented in the present specification and claims are shown in conventional format wherein the amino group at the N-terminus appears to the left and the carboxyl group at the C-terminus at the right. Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y) and valine (Val;V). For purposes of the present invention the term "mature EPSP synthase" relates to polypeptide without the N-terminal chloroplast transit peptide. It is now known that the precursor form of the EPSP synthase in plants (with the transit peptide) is expressed and upon delivery to the chloroplast, the transit peptide is cleaved yielding the mature EPSP synthase. All numbering of amino acid positions are given with respect to the mature EPSP synthase (without chloroplast transit peptide leader).

FIG. 1 shows the amino acid sequence for EPSP synthase from various plant and bacterial species. In FIG. 1, an "X" in the sequence denotes that the amino acid at that position is unknown. A "." represents a space inserted to accomodate lineup of the sequences. Inspection of the sequences and alignment to maximize the similarity of sequence reveals regions of conserved amino acid residues (indicated by the consensus sequence) in the regions where the alanine for glycine substitution and threonine for alanine substitution are made. Indeed, all monofunctional EPSP synthase enzymes reported in the literature and in the present specification reveal a glycine and an alanine at the two positions in the conserved regions. Those familiar with the literature will recognize that some organisms, such as yeast and molds (*Aspergillus sp*) have a multifunctional "arom complex" which includes an EPSP synthase component. The noted amino acids are also conserved and introduction of the described substitutions in the EPSP synthase component of the multifunctional "arom complex" should also result in the glyphosate-tolerant activity.

Specifically, the glycine residue which is replaced by the alanine residue in the preparation of the glyphosate-tolerant EPSP synthases of the present invention occurs at position 101 in the EPSP synthase of petunia; position 101 in the EPSP synthase of tomato; position 101 in the EPSP synthase of *Arabidopsis thaliana*; position 101 in the EPSP synthase of *Brassica napus*; position 104 in the EPSP synthase of *Glycine max*; position 96 in the EPSP synthase of *E. coli* K-12 (Duncan et al., 1984) and position 96 in the EPSP synthase of *Salmonella typhimurium* (Stalker et al., 1985). The alanine residue which is replaced by the threonine residue in the preparation of the glyphosate-tolerant EPSP synthases of the present invention occurs at position 192 in the EPSP synthase of petunia; position 192 in the EPSP synthase of tomato; position 192 in the EPSP synthase of *Arabidopsis thaliana*; position 192 in the EPSP synthase of *Brassica napus*; at position 195 in the EPSP synthase of *Glycine max*; position 183 in the EPSP synthase of *E. coli* K-12 and position 183 in the EPSP synthase of *Salmonella typhimurium*. These examples demonstrate that the alanine for glycine and threonine for alanine replacements can be introduced into the conserved regions of these other wild-type EPSP synthase enzymes to yield glyphosate-tolerant EPSP synthase enzymes.

Hence, in one aspect the present invention provides a gene encoding a glyphosate-tolerant EPSP synthase enzyme and a method for producing such a gene which comprises substituting an alanine residue for the second glycine residue in a first conserved region having the sequence:

-L-G-N-A-G-T-A-
located between positions 80 and 120 in the mature wild-type EPSP synthase amino acid sequence, and substituting a threonine for an alanine in a second conserved region having the sequence:

-A-L-L-M-x₁-A-P-L-A- located between positions 170 and 210 in the mature wild-type EPSP synthase amino acid sequence where x₁ is either A (alanine), S (serine) or T (threonine). In most cases the first conserved region will be located between positions 90 and 110 and the second conserved region between positions 175 and 200 in the mature EPSP synthase.

In one embodiment, glyphosate-tolerant EPSP synthase coding sequences are useful in further enhancing the efficacy of glyphosate-tolerant transgenic plants. Methods for transforming plants to exhibit glyphosate tolerance are disclosed in European Patent Office Publication No. 0218571 and commonly assigned U.S. Pat. No. 4,940,835 entitled "Glyphosate-Resistant Plants", issued Jul. 10, 1990, the disclosures of which are specifically incorporated herein by reference. The present invention can be utilized in this fashion by isolating the plant or other EPSP synthase coding sequences and introducing the necessary change in the DNA sequence coding for EPSP synthase to result in the aforementioned substitutions in the translated EPSP synthase enzyme.

In another aspect, the present invention provides a transformed plant cell and plant regenerated therefrom which contain a plant gene encoding a glyphosate-tolerant EPSP synthase enzyme having a first sequence:

-L-G-N-A-A-T-A- located between positions 80 and 120 in the mature EPSP synthase amino acid sequence and having a second sequence:

-A-L-L-M-x₁-A-P-L-T located between positions 170 and 210 in the mature EPSP synthase amino acid sequence where x₁ is either A (alanine), S (serine) or T (threonine). In most cases the first sequence will be located between positions 90 and 110 and the second sequence will be located between 175 and 200 in the mature EPSP synthase. The gene further comprises a DNA sequence encoding a chloroplast transit peptide attached to the N-terminus of the mature EPSP synthase coding sequence, said transit peptide being adapted to facilitate the import of the EPSP synthase enzyme into the chloroplast of a plant cell.

Therefore, in yet another aspect the present invention also provides a plant transformation or expression vector comprising a plant gene which encodes a glyphosate-tolerant EPSP synthase enzyme having a first sequence:

-L-G-N-A-A-T-A- located between positions 80 and 120 in the mature EPSP synthase amino acid sequence and having a second sequence:

-A-L-L-M-x₁-A-P-L-T located between positions 170 and 210 in the mature EPSP synthase amino acid sequence where x₁ is either alanine, serine or threonine.

According to still another aspect of the present invention, a process is provided that entails cultivating such a plant and, in addition, propagating such plant using propagules such as explants, cuttings and seeds or crossing the plant with another to produce progeny that also display resistance to glyphosate herbicide.

In yet another aspect, the present invention provides a method for selectively controlling weeds in a field containing a crop having planted crop seeds or plants by planting crop seeds or plants which are made glyphosate tolerant by containing a gene encoding a glyphosate tolerant EPSPS enzyme which contains the amino acid sequence -L-G-N-A-A-T-A- between positions 80 and 120 in the mature EPSPS sequence and the amino acid sequence -A-L-L-M-x₁-A-P-L-T- in A-P-L-T- in a second conserved region between positions 170 and 210 in the mature EPSPS amino acid sequence where x₁ is either alanine, serine or threonine and subsequently applying to the crop and weeds a sufficient amount of glyphosate to control the weeds without significantly affecting the crop. As a result, a glyphosate containing herbicide can be applied to a field where plants containing the glyphosate tolerant EPSP synthase gene are growing to selectively kill or control weeds that may also be growing in the field that are not glyphosate tolerant. This allows the desired glyphosate tolerant crop plants to take full advantage of the available nutrients in the field for an improved crop quality and yield.

The EPSP synthase sequences shown in FIG. 1 represent a broad evolutionary range of source materials for EPSP synthases. These data demonstrate that EPSP synthase from bacterial and plant material contain the aforementioned conserved regions. However, those skilled in the art will recognize that a particular EPSP synthase may be produced by and isolated from another source material which may not have the exact sequence of the conserved region. Indeed, it has been found that an alanine may be inserted for the first glycine of the conserved region of petunia EPSP synthase with no attendant changes in glyphosate sensitivity.

A threonine substitution for the alanine residue in the afore-described second conserved region results in a glyphosate resistant EPSP synthase and is the most preferred substitution. Those skilled in the art will recognize that substitutions of other amino acid residues are likely to yield EPSP synthases which are still glyphosate tolerant and possess a $K_m$ sufficient to maintain catalytic activity. Hence, other substitutions at this position should be considered within the spirit and scope of the present invention. In fact, substituting either serine, glycine, proline, asparagine, aspartic acid, lysine or phenylalanine for the alanine residue in the afore-described second conserved region results in a functional, glyphosate resistant EPSP synthase which is able to complement E. coli aroA and support E. coli cell growth on minimal medium containing glyphosate. The serine, glycine, proline and aspartic acid substitutions produce an EPSP synthase which must be expressed from very strong bacterial promoters, such as lambda $P_L$, for complementation of E. coli aroA. Those variants have been assayed for EPSP synthase activity. Both the proline and aspartic acid variants have very little enzyme activity, but do produce an intact EPSP synthase based on western blot analysis. The asparagine, lysine and phenylalanine variants were able to complement E. coli aroA and support cell growth on minimal medium containing glyphosate.

The glyphosate-tolerant EPSP synthase plant gene encodes a polypeptide which contains a chloroplast transit peptide (CTP), which enables the EPSP synthase polypeptide to be transported into a chloroplast inside the plant cell. The EPSP synthase gene is transcribed into mRNA in the nucleus and the mRNA is translated into a precursor polypeptide (CTP/mature EPSP synthase) in the cytoplasm. The precursor polypeptide is transported (imported) into the chloroplast at which time the CTP is cleaved to produce the mature EPSP synthase enzyme. Suitable CTPs for use in the present invention may be obtained from various sources. Most preferably, the CTP is obtained from the endogenous EPSP synthase gene of the subject plant to be transformed. Alternately, one may also use a CTP from an EPSP synthase gene of another plant. Although there is little homology between the CTP sequences of the EPSP synthase gene and the ssRUBISCO gene (see e.g., Broglie, 1983), one may find that non-homologous CTPs may function in particular embodiments. Suitable CTP sequences for use in the present invention can be easily determined by assaying the chloroplast uptake of an EPSP synthase polypeptide comprising the CTP of interest as described hereinafter. It has been found that where a CTP is used other than the CTP of the EPSPS gene, one may need to include a small part of the N-terminus of the source protein from which the CTP is derived to obtain efficient import of the EPSP synthase into the chloroplasts. In most cases, one would preferably isolate the EPSPS gene from the plant to be transformed and introduce the substitutions of the present invention into a cDNA construct made from the endogenous EPSPS mRNA of the subject plant. Suitable plants for the practice of the present invention include, but are not limited to, soybean, cotton, alfalfa, oil seed rape, flax, tomato, sugar beet, sunflower, potato, tobacco, maize, wheat, rice, lettuce, as well as tree species such as poplar, pear and apple, nut bearing plants and vine plants such as grape.

Promoters which are known or found to cause transcription of the EPSP synthase gene in plant cells can be used in the present invention. Such promoters may be obtained from plants, plant pathogenic bacteria or plant viruses and include, but are not necessarily limited to, the 35S and 19S promoters of cauliflower mosaic virus, the full-length transcript promoter from the figwort mosaic virus, promoters isolated from plant genes such as EPSP synthase, ssRUBISCO genes and promoters obtained from T-DNA genes of *Agrobacterium tumefaciens* such as nopaline and mannopine synthases. The particular promoter selected should be capable of causing sufficient expression to result in the production of an effective amount of glyphosate-tolerant EPSP synthase polypeptide to render the plant cells and plants regenerated therefrom substantially resistant to glyphosate. Those skilled in the art will recognize that the amount of glyphosate-tolerant EPSP synthase polypeptide needed to induce tolerance may vary with the type of plant.

The promoters used for expressing the EPSP synthase gene of this invention may be further modified if desired to alter their expression characteristics. For example, the CaMV35S promoter may be ligated to the portion of the ssRUBISCO gene which represses the expression of ssRUBISCO in the absence of light, to create a promoter which is active in leaves but not in roots. The resulting chimeric promoter may be used as described herein. As used herein, the phrase "CaMV35S" promoter includes variations of CaMV35S promoter, e.g. promoters derived by means of ligation with operator regions, random or controlled mutagenesis, addition or duplication of enhancer sequences, etc. One particularly useful promoter is the full length transcript promoter from the figwort mosaic virus (FMV) (Gowda, 1989).

Variant EPSP synthases which contain only the glycine to alanine change at position 101 as described above are highly resistant to glyphosate. However, this resistance is accompanied by an increase in the binding constant ($K_m$) for phosphoenolpyruvate (PEP), one of the two natural substrates for the enzyme. The binding constant for the other substrate, shikimate-3-phosphate (S3P), is not affected. For example, the wild type petunia EPSP synthase has a binding constant ($K_i$) for the competitive inhibitor glyphosate of 0.4 $\mu$M and a $K_m$ for PEP of 5.2 $\mu$M, while the variant form with the alanine for glycine substitution at position 101 has a $K_i$ for glyphosate of 2000 $\mu$M and a $K_m$ for PEP of 198 $\mu$M. Because of the elevated $K_m$ for PEP, normal catalytic activity will only be achieved at physiological concentrations of PEP by an elevated level of the variant enzyme. If a variant of EPSP synthase could be identified that had a high $K_i$ for glyphosate and a lower $K_m$ for PEP, such a variant would enhance the ability to achieve glyphosate tolerance in plant species or plant tissues where it is difficult to engineer a high level of gene expression.

Selecting for new glyphosate-tolerant EPSP variants in bacteria would allow a much larger number of organisms to be screened in a shorter amount of time than would be possible in selections with higher organisms. The petunia EPSP synthase cDNA clone can be expressed in *E. coli* to produce a fully functional EPSP synthase enzyme when the cDNA clone is properly tailored for expression in *E. coli.*, so to hasten the isolation of variants a system for the expression and selection of variant forms of petunia EPSP synthase was developed in the common laboratory organism *E. coli*.

General Features of Selection Scheme for Identifying Glyphosate Resistant Variants with Low $K_m$ Values for PEP

| Component | Features |
| --- | --- |
| *E. coli* Host | aroA- strain or prototrophic strain with endogenous EPSPS activity inhibited with low levels of glyphosate (empirically determined for each host). |
| Expression Plasmid | Self replicating plasmid with a weak bacterial promoter fused to a plant EPSPS gene, which is not able to complement the *E. coli* aroA mutation and support cell growth on minimal medium when expressed at a weak level. The promoter should be weak enough so that a fusion with a wild type EPSPS gene would be inhibited at a concentration of glyphosate similar to that needed to inhibit the endogenous bacterial EPSPS. |
| Mutagens | Should create point mutations, either single or multiple, transitions or transversions, but not insertions, deletions or frameshifts. Spontaneous mutations could also be selected, but would probably be less efficient. |
| Selection Medium | Minimal bacterial growth medium containing essential salts and minerals and sugars without aromatic amino acids. Antibiotics may be added which correspond to the drug resistance marker genes on the expression plasmid to select only for bacterial cells containing the expression plasmid. For aroA hosts, glyphosate is not required to select for variants with low $K_m$ values for PEP, which are able to complement the *E. coli* aroA mutation when expressed at a weak level. For prototrophic *E. coli* strains, add glyphosate to inhibit the endogenous EPSPS activity. |

Exemplary Heterologous Bacterial Expression/ Selection System

A) Construction of pMON342 and pMON9566 expression vectors for wild type and variant petunia EPSP synthases in *E. coli*.

Plasmid pMON342 carries the "mature" wild-type petunia EPSP synthase coding sequence (without chloroplast transit peptide) expressed from tandem copies of the bacteriophage lambda pL promoter (double pL). This plasmid was derived from pMON9531 and pMON9556, petunia EPSP cDNA clones, as described below (the isolation of pMON9531 and pMON9556 is described hereinafter).

A unique NcoI site and ATG translational initiation signal were introduced at the amino terminus of the wild-type petunia EPSP synthase cDNA coding sequence for the mature protein. Simultaneously, the chloroplast transit peptide coding sequence was removed by subjecting M8017 (the M13mp9 clone of the 300 bp EcoRI cDNA fragment of pMON9531) to site directed. mutagenesis using the procedure of Zoller and Smith (1983) and the following mutagenesis primer:

5'-ATCTCAGAAGGCTCCATGGTGCTGTAGCCA-3'

A variant phage clone was isolated that contained an NcoI site. The presence of the above-described mutation was confirmed by sequence analysis. This M13mp9 clone was designated M8019.

Plasmid pMON6001 is a derivative of pBR327 (Soberon et al., 1980) carrying the *E. coli* K12 EPSP synthase coding sequence expressed from two tandem copies of a synthetic bacteriophage lambda pL promoter. Plasmid pMON6001 was constructed in the following manner. First, pMON4 (Rogers et al., 1983) was digested with ClaI and the 2.5 kb fragment was inserted into a pBR327 plasmid vector that had also been cleaved with ClaI. The resulting plasmid, pMON8, contains the EPSP synthase coding sequence reading in the same direction as the beta-lactamase gene of pBR327.

To construct pMON25, a derivative of pMON8 with unique restriction endonuclease sites located adjacent to the *E. coli* EPSP synthase coding sequence, the following steps were taken. A deletion derivative of pMON4 was made by cleavage with BstEII and religation. The resultant plasmid pMON7 lacks the 2 kb BstEII fragment of pMON4. Next, a 150 bp HinfI to NdeI fragment which encodes the 5' end of the EPSP synthase open reading frame was isolated after digestion of pMON7 with NdeI and HinfI and electroelution following electrophoretic separation on an acrylamide gel. This piece was added to the purified 4.5 kb BamHI-NdeI fragment of pMON8 which contains the 3' portion of the EPSP synthase coding sequence and a synthetic linker with the sequence:

5'-GATCCAGATCTGTTGTAAGGAGTCTAGACC-ATGG-3'

3'-GTCTAGACAACATTCCTCAGATCTGGTACC-TTA-5'

The resulting plasmid pMON25 contains the *E. coli* EPSP synthase coding sequence preceded by unique BamHI and BglII sites, a synthetic ribosome binding site, and unique XbaI and NcoI sites, the latter of which contains the ATG translational initiation signal of the coding sequence.

To construct pMON6001, pMON25 was digested with BamHI and mixed with a synthetic DNA fragment containing a partial phage lambda pL sequence (Adams and Galluppi, 1986) containing BamHI sticky ends:

5'-GATCCTATCTCTGGCGGTGTTGACATAAATAC-CACTGGCGGTGATACTGAGCACATCG-3'

3'-GATAGAGACCGCCACAACTGTATTTATGGTGA-CCGCCACTATGACTCGTGTAGCCTAG-5'

The resulting plasmid pMON6001 carries two copies of the synthetic phage lambda pL promoter fragments as direct repeats in the BamHI site of pMON25 in the correct orientation to promote transcription of the *E. coli* EPSP synthase coding sequence.

Plasmid pMON6001 was cleaved with NcoI and EcoRI and the 3 kb fragment isolated from an agarose gel. This fragment was mixed with the small 100 bp NcoI-EcoRI fragment purified from M8019. Following ligation and transformation a clone was identified that contained the small 100 bp NcoI-EcoRI fragment corresponding to the 5' end of the "mature" EPSP synthase of petunia. This construct was designated pMON9544.

Plasmid pMON9544 was digested with EcoRI and treated with alkaline phosphatase. The EcoRI fragment of pMON9544 was mixed with pMON9556 DNA that had been cleaved with EcoRI to release a 1.4 kb fragment encoding the 3' portion of the petunia EPSP synthase coding sequence. Following ligation and transformation, a clone was identified that could complement an *E. coli* aroA mutation and carried the 1.4 kb fragment of pMON9556 to give an intact mature coding sequence for petunia EPSP synthase. This plasmid was designated pMON342.

The EcoRI site at the 3' end of the EPSP synthase in pMON342 was replaced with a ClaI site to facilitate construction. This was accomplished by partial digestion with EcoRI followed by digestion with mungbean nuclease to make the ends blunt. ClaI linkers (5'-CATCGATG-3', New England Biolabs) were added to the blunt ends by ligation with T4 DNA ligase. The mixture was digested with ClaI to produce sticky ends, and the 5 kb EcoRI partial digest was isolated from an agarose gel and ligated with T4 DNA ligase. This plasmid was designated pMON9563.

A 29-nucleotide mutagenic deoxyoligonucleotide having the following sequence:

5'-GCCGCATTGCTGTAGCTGCATTTCCAAGG-3' was synthesized for introducing the alanine for glycine substitution at position 101 using an automated DNA synthesizer (Applied Biosystems, Inc.). The deoxyoligonucleotide was purified by preparative polyacrylamide gel electrophoresis.

The 660 bp EcoRI-HindIII fragment of pMON9563 was subcloned into an EcoRI-HindIII digested M13mp10 bacteriophage vector (New England Biolabs). The single-stranded template DNA was prepared from the subclone as described in the M13 cloning and sequencing handbook by Amersham, Inc. (Arlington Heights, Ill.) and oligonucleotide mutagenesis reactions were performed as described by Zoller and Smith (1983) using the oligonucleotide described above. This plasmid was designated M9551. The 660 bp EcoRI-HindIII fragment of M9551 was inserted into pMON9563 between the EcoRI and HindIII sites, replacing the corresponding wild type fragment. This plasmid was designated pMON9566.

The double pL promoter used to express the petunia EPSP synthase in pMON342 and pMON9566 leads to a very high level of expression of the enzyme. The enzyme is present at such high concentration that bacteria harboring either of these plasmids are tolerant to very high levels of glyphosate (>5 mM) in growth media, even though the enzyme produced by pMON342 is the wild type form. In order to produce a plasmid that would allow for selection of glyphosate tolerant forms of the enzyme it was necessary to replace the high expressing lambda phage pL promoter with a much weaker promoter sequence. A plasmid for identifying such a promoter was constructed as follows: pMON9544, the precursor to pMON342, was digested with BamHI to remove the pL promoters, and was recircularized by ligation resulting in pMON362. The EcoRI fragment of pMON9556 containing the 3'portion of the petunia EPSPS cDNA was then inserted into the EcoRI site of this plasmid reconstituting the entire coding sequence. The resulting plasmid, pMON364 is identical to pMON342 except that there is no promoter 5' of the EPSP synthase coding sequence.

To facilitate future cloning steps, the EcoRI/PstI fragment of pMON364 from which the promoter elements had been deleted was ligated to the EcoRI/PstI fragment of pMON9563 containing most of the EPSP synthase cDNA creating pMON9564. This plasmid is identical to pMON364 except that it has a unique ClaI site at the 3'-end of the EPSP synthase cDNA and a unique EcoRI site within the EPSP synthase coding sequence. Transformation of an aroA *E. coli*, such as SR481 (Bachman et al., 1980; Padgette et al., 1987) failed to complement the mutation, thus demonstrating the effective deletion of the promoter region and the inability of this plasmid to produce EPSP synthase in *E. coli*. An empirical screening approach was used to isolate promoters with an appropriate low level expression in *E. coli* as follows.

B) Generation of a series of promoter constructs.

Chromosomal DNA isolated from the *E. coli* strain SR20 (GM42 hfr, his-, dam3-) was digested completely with MboI. The MboI fragments were cloned into the BglII site of plasmid pMON9564. The BglII site is in a multilinker located upstream of the promoterless petunia EPSPS coding sequence which had been tailored for expression in *E. coli*. The ligation mixture was used to transform *E. coli* strain SR481, the aroA- variant lacking endogenous EPSPS activity. Forty-one colonies were obtained which contained MboI fragments with sufficient promoter activity to express the petunia EPSPS cDNA, complementing the aroA defect in SR481 and supporting cell growth on minimal medium. The 41 colonies were streaked individually onto MOPS minimal medium containing glyphosate at 1, 5, 10, 15 and 20 mM concentrations. The amount of cell growth on increasing concentrations of glyphosate was used as a measure of the relative promoter strength of each MboI fragment expressing the petunia EPSPS coding sequence. To further characterize each of the MboI promoter fragments, plasmid miniprep DNA was prepared by the alkaline lysis method from each of the 41 colonies and was digested individually with EcoRI, BamHI, HindIII, ClaI and NcoI. Those restriction enzymes were chosen because they cut within, or flank the petunia EPSPS coding sequence and would be used for mobilizing mutagenized fragments. Therefore, ideal promoter fragments would not contain restriction sites for any of those enzymes. There were 8 MboI fragments with varying degrees of promoter activity which lacked restriction sites for the enzymes listed above. Two of them, pMON8105 and pMON8143, were selected for further characterization. Both plasmids complemented the aroA defect and supported the growth of SR481 on minimal medium containing up to 1 mM (pMON8105) and 20 mM (pMON8143) glyphosate.

C) Testing the Expression Vectors.

The heterologous expression system was tested with a known variant to see if glyphosate resistant variants of petunia EPSPS could be selected. The glyphosate resistant mutation, glycine (101) to alanine, was introduced into the petunia EPSPS coding sequence of both pMON8105 and pMON8143 expression vectors to generate pMON8135 and pMON8152, respectively. That was achieved by replacing the 660 bp EcoRI-HindIII region from both vectors with the 660 bp EcoRI-HindIII region from pMON9566 which contained the glycine (101) to alanine mutation. Both pMON8135 and pMON8152 were used to transform SR481. The pMON8152 construct was able to complement the aroA defect in SR481 and support cell growth on minimal medium containing up to 50 mM glyphosate.

The weakly expressing pMON8135 (FIG. 2) construct containing the known variant enzyme sequence was not able to complement the aroA defect in SR481 and did not support cell growth on minimal medium. A culture of SR481 cells carrying the pMON8135 plasmid was assayed to demonstrate that the petunia EPSP synthase enzyme was expressed. Plasmid pMON8135 has a specific activity of 41 nmol/minute/mg protein and pMON8105 has a specific activity of 28 nmol/minute/mg protein. Thus, the pMON8135 construct was expressed in *E. coli* with a specific activity similar to its parental construct pMON8105. It was then hypothesized that the elevated $K_m$ for PEP of the variant enzyme (198 $\mu$M versus 5.2 $\mu$M for the wild type) resulted in a relatively inefficient EPSP synthase enzyme that was unable to support the growth of the aroA mutant when the enzyme was produced at this low level. This result demonstrated the importance of the $K_m$ for PEP and the ability of a variant petunia EPSPS enzyme to complement aroA when weakly expressed in *E. coli*. If a variant enzyme has a high $K_m$ for PEP, then a greater level of expression is required to complement aroA. The weakly expressing vector, pMON8105, therefore, provides a novel, powerful selection tool for identifying petunia EPSPS variants which have relatively low $K_m$ values for PEP. In combination with glyphosate selection, variants which combine significant glyphosate tolerance with low $K_m$ values for PEP can be obtained. This implies that not only can new variants of the wild type enzyme be obtained from this system, but it can also be used to select for second site mutations in the glycine (101) to alanine variant coding sequence that lower the $K_m$ for PEP while maintaining glyphosate tolerance. This unexpectedly powerful selection system constitutes one part of the present invention. Those skilled in the art will recognize that one can use other strains of aroA bacteria, other methods of insertion, other sources of random DNA fragments and coding sequences from organisms other than petunia while not departing from the spirit and scope of the invention.

D) Construction of pMON8205 vector

Plasmid pMON8205 was constructed by replacing the 994 bp 3' half of the EPSPS coding sequence and 3' untranslated region between the HindIII and ClaI sites in the pMON8135 vector with the same region from pMON953. This provided an expression vector containing the petunia EPSPS glycine 101 to alanine coding sequence with the internal NcoI site deleted, making the NcoI at the start of the gene unique to aid in subsequent subcloning steps. Also, a unique XbaI site was provided at the 3' end of the gene, after the translational stop site to also aid in subsequent subcloning steps.

The internal NcoI site was eliminated and the XbaI site was created in the EPSPS coding sequence by 2 site directed mutageneses to create pMON953 as follows. The 994 bp HindIII-ClaI fragment containing the 3' end of the petunia EPSPS coding sequence and 3' untranslated region from pMON9566 was subcloned into the Bluescript pBSKS+ vector to create pMON9763. A single strand DNA template was prepared and an XbaI site was introduced by site directed mutagenesis using the method of Kunkle and the following synthetic DNA oligonucleotide primer:

5'-GAACCGCTTCCCTATATTCTAGAATGTAAGTAA-3'

The resulting plasmid was pMON9766. To remove the NcoI site in the petunia EPSPS, a single strand template was prepared from pMON9766 for site directed mutagenesis. The synthetic oligonucleotide that was used in the mutagenesis has the following sequence:

5'-GATCACAGGATGGCAATGGCTTTTTCTCTT-3'

The resulting plasmid which contains the NcoI deletion is pMON950. The 1.00 kb HindIII-ClaI petunia EPSPS fragment from pMON950, was fused to the 4.08 kb HindIII-ClaI fragment of pMON9731 which contains the rest of the wild type petunia EPSPS gene. The resulting plasmid, pMON953, contains the reconstructed wild type petunia EPSPS gene with the internal NcoI site deleted, the chloroplast transit peptide, G10 leader, and PrecA promoter for *E. coli* expression.

E) In vivo Mutagenesis of pMON8205 with N-methyl-N'-nitro-N-Nitrosoguanidine (NG)

The following mutagenesis procedure serves as an example of the application of this selection system for obtaining such second site variants of the glycine (101) to alanine variant of the petunia EPSPS enzyme. N-methyl-N'-nitro-N-Nitrosoguanidine (NG) is a powerful methylating compound commonly used in bacterial genetics as a mutagen. It primarily induces GC→AT base transitions, however, AT→GC transitions, transversions and frame shift mutations can also be induced. Plasmid pMON8205 was transformed into *E. coli* JM101. A 4 ml culture was grown overnight to saturation in 2XYT medium containing 50 $\mu$g/ml carbenicillin. The culture was split into 4 duplicate 1 ml aliquots. Each aliquot was then diluted 40 fold with 40 ml of 2XYT medium and placed in a 250 ml Klett side arm flask. The 4 duplicate Klett flasks were then shaken continuously in a water bath at 37° C. and the growth was monitored with a Klett-Summerson photoelectric colorimeter until the cultures had grown to a Klett value of approximately 110 Klett units. The cells were then harvested by pelleting the cells in Oakridge screwcap tubes in a centrifuge by spinning them at 7,000 rpm for 5 minutes at 5° C. Each cell pellet (4 total) was washed twice with 40 ml 0.1M sodium citrate, pH 5.5 and pelleted as above after each wash. Each cell pellet was resuspended in 32 ml 0.1M sodium citrate, pH5.5 and 1.6 ml of a 1 mg/ml NG (Sigma Chemical Co., St. Louis, Mo.) stock made in 0.1M sodium citrate pH5.5 buffer was added to each of the 4 duplicate samples.

The final concentration of NG in each of the 4 duplicate samples was 50 $\mu$g/ml. The samples were then incubated at 37° C. for 5, 10, 20 or 30 minutes. The cells were pelleted from each sample as described above. The cell pellets were then washed twice, each time with 30 ml of 0.1M phosphate buffer pH7.0 and pelleted after each wash. The pellets were then resuspended and pooled together in a final volume of 250 ml 2XYT. The culture was then shaken continuously in a water bath at 37° C. for a total of 2.5 hours. The cells were then harvested by pelleting in a 500 ml centrifuge bottle and spinning them for 10 minutes at 7,000 rpm at 5° C. in a Beckman JA10 rotor. The cell pellet was then frozen at −20° C. The pellet was then thawed and the mutagenized pMON8205 plasmid DNA was extracted following a standard alkaline lysis procedure.

F) Screening for Glyphosate Resistant Coding Sequence Variants.

A multi-step screening procedure was used to identify glyphosate resistant variants of petunia EPSPS. The first screening step involved the transformation of *E. coli* with the NG mutagenized pMON8205 plasmid DNA and selecting for glyphosate resistant colonies on minimal medium containing glyphosate. The SR481 aroA− *E. coli* strain had a very low transformation frequency, yielding at best $10^4$ transformants per $\mu$g of plasmid DNA. To overcome that problem, the *E. coli* strain JM101 was used because transformation efficiencies of up to $10^8$ transformants per $\mu$g of plasmid DNA could be routinely obtained. However, JM101 contained a fully functional aroA gene and was able to grow on MOPS minimal medium. By plating JM101 on minimal medium plates containing increasing concentrations of glyphosate, it was determined that 2 mM glyphosate would inhibit the endogenous EPSP synthase enzyme activity and growth of JM101 on minimal media. Since the weakly expressing wild type petunia EPSP synthase cDNA construct (pMON8105) could not support the growth of the aroA− *E. coli* strain, SR481, on 1 mM glyphosate and the corresponding glycine 101 to alanine construct (pMON8135) could not complement the bacterial aroA, then a prototrophic strain of *E. coli* can be used for the selections if the glyphosate concentrations are greater than 2 mM. The NG mutagenized pMON8205 plasmid DNA was transformed into JM101 and glyphosate resistant variants were selected on MOPS minimal medium containing 10 mM glyphosate.

The glyphosate resistant colonies contained pMON8205 plasmids with a variety of mutations, including promoter mutations, copy number mutations and glyphosate resistant mutations in the petunia EPSP synthase coding sequence. Mutations that increased plasmid copy number or increased the strength of the promoter that was used to drive the EPSP synthase gene would increase the amount of EPSP synthase enzyme in the bacteria and would confer an aroA positive glyphosate tolerant phenotype to the cells. To eliminate mutations in the non-coding regions of the NG mutagenized pMON8205 plasmid, the glyphosate resistant colonies were pooled together into 2XYT liquid media containing 50 $\mu$g/ml carbenicillin and grown overnight at 37° C. with agitation to aerate the cells. The cells were then pelleted from the saturated cultures by centrifugation and the plasmid DNA was extracted using the alkaline lysis procedure. The plasmid DNA was then digested completely with NcoI and ClaI enzymes and the 1.73 kb petunia EPSPS coding sequence region was then purified out of a 0.8% SeaPlaque (FMC Corporation) low gelling temperature agarose gel. The 1.73kb NcoI-ClaI fragment was used to replace the analogous fragment containing the wild-type coding sequence in the non-mutagenized pMON8105 expression vector by ligating it to the 3.62kb NcoI-ClaI vector fragment of this plasmid which had been isolated as above. The ligation mixture was then used to transform JM101 cells, which were plated onto MOPS minimal medium containing 10 mM glyphosate to select for glyphosate resistant mutations in the petunia EPSP synthase coding sequence region.

The glyphosate resistant colonies obtained from the transformations of the sub-cloned coding region were further characterized by measuring the rate of growth of each variant in liquid culture in varying concentrations of glyphosate. This growth curve analysis functioned as a tertiary screen and was performed in the following manner.

Glyphosate resistant colonies were picked off the selection plates and inoculated individually into precultures containing 1 ml of MOPS medium and 50 $\mu$g/ml carbenicillin. The precultures were then grown to saturation by shaking the cultures overnight at 370° C. The next morning the density of each culture was determined by withdrawing a 100 $\mu$l aliquot from each and diluting it 10 fold with the addition of 900 $\mu$l MOPS medium, then reading the optical density at a wavelength of 660 nm in a spectrophotometer. The saturated precultures were then diluted to 1% by adding 50 $\mu$l from each saturated preculture to 5 ml of MOPS media containing 0, 5 or 10 mM glyphosate. The diluted precultures were grown in glass culture tubes fitted with stainless steel closures, rotating on a wheel at 37° C. The glass culture tubes were designed for direct reading in a Klett-Summerson photoelectric colorimeter, which was used to monitor the growth of the bacterial cultures at approximately 3 hour intervals.

One culture, designated #742, was identified which grew very fast in MOPS medium containing 10 mM glyphosate. Culture #742 grew 64% as well as the petunia EPSPS GA101 GD144 positive control culture for the media and significantly better than the other glyphosate resistant cultures tested. The petunia EPSPS GA101 GD144 control culture represents a variant of the EPSPS gene that has a glycine to alanine substitution at position 101 and a glycine to aspartic acid substitution at position 144. This variant is described in co-pending and commonly assigned U.S. patent application Ser. No. 07/380,963, entitled "Glyphosate-Tolerant 5-Enolpyruvyl-3-Phosphoshikimate Synthases" which is hereby incorporated by reference.

G) Characterization of the Glyphosate Resistant Coding Sequence Variants.

The balance of the #742 preculture (~750 μl) was used to inoculate 2 ml of 2XYT medium containing 50 μg/ml carbenicillin and was shaken overnight at 37° C. to reach saturation. Plasmid DNA was isolated from an aliquot of the saturated culture using an alkaline lysis procedure. The plasmid was designated pMON8252. An aliquot of the pMON8252 plasmid was used to transform the E. coli host SR481 (described above) and reselected on MOPS medium containing 10 mM glyphosate and 50 μg/ml carbenicillin. A single glyphosate resistant colony of pMON8252 was picked off the selection plate and used to inoculate 3 ml of 2XY1 bacterial medium containing 50 μg/ml carbenicillin. The culture was then aerated on a rotating wheel at 37° C. until saturated and then used to inoculate a larger 250 ml culture. The large culture was grown to saturation by continuously shaking it overnight at 37° C. in a water bath. The bacterial cells were lysed and the extracts were assayed for EPSPS activity.

Specifically, the bacterial cell paste was washed twice with 0.9% saline, suspended in buffer (100 mM Tris-HCl, 5 mM benzamidine HCl) and passed twice through a French Pressure Cell at 1000 psi. The cell extract was separated from the cells by centrifuging at 15,000×gravity for 10 minutes at 5° C. It was desalted using Sephadex G-50 (Pharmacia, Piscataway, N.J.). The desalted extract was assayed for EPSP synthase activity as follows.

To an assay mix (40 μl) containing shikimate-3-phosphate (2 mM), $^{14}$C-phosphoenolpyruvate (1 mM, 1.2 mCi/mmol), ammonium molybdate (0.1 mM), potassium fluoride (5 mM) in 50 mM HEPES-KOH, pH 7, was added 100 μl of the extract and incubated at 25° C. for 2 minutes. The reaction was quenched by the addition of 50 μl of 90% ethanol/0.1M acetic acid, pH 4.5. Seventy μl of the reaction mixture was loaded on a SynchroPak AX100 HPLC column (0.4×25 cm) and the column was eluted with 0.5M potassium phosphate, pH 5.5 at 1 ml/minute. The radioactivity of the eluent was monitored using a Radiomatic Flo-One Beta Instrument (Radiomatics, Florida). The EPSP synthase activity was determined by measurement of the conversion of $^{14}$C-PEP to $^{14}$C-EPSP synthase, both of which are resolved under the above conditions of chromatography. The protein content of the extract was determined by the method of Bradford (Biorad Labs, California). The specific activity of the extract is expressed as nanomoles of EPSP synthase formed/minute/mg protein.

Kinetic constants (appK$_m$ PEP and appK$_i$ glyphosate) were determined for EPSP synthase as described below. Substrate kinetic parameters were determined at pH 7.9 in 50 mM HEPES (N-[2-hydroxyethyl]piperazine-N'-[2-ethanesulfonic acid]) buffer in the presence of 2 mM S3P and varying amounts of $^{14}$C-PEP (10 μM–400 μM), for 2.0 minutes at 25° C. Reactions were quenched with 100 mM NaAcetate in ethanol, pH 4.5, centrifuged and analyzed for product EPSP formation by HPLC with flow radioactivity detection. HPLC conditions were 0.35M KPi, pH 6.5, on a Synchropak AX100 column at 1.0 ml/minute. The resulting rates were plotted by hyperbolic plot, Lineweaver-Burk plot and Eadie-Hofstee plot and an average K$_m$ for PEP value obtained. The appK$_i$ for glyphosate versus PEP was determined as described for the substrate kinetic constant except in the presence of varying concentrations of glyphosate (0,100,200,400 μM). Initial rate data was plotted as 1/[PEP] versus 1/V and the slopes of the resulting lines were replotted versus [glyphosate].

The assay results showed that the bacterial cells containing the pMON8252 plasmid had an EPSP synthase activity of 33 nmoles of EPSP formed/minute/mg of protein. The enzyme was highly resistant to glyphosate as indicated by a K$_i$ for glyphosate of 683 μM. The K$_m$ for PEP was determined to be 54 μM. The petunia EPSPS glycine (101) to alanine variant has a K$_i$ for glyphosate of 2000 μM and a K$_m$ for PEP of 200 μM. The K$_i$/Km ratio for the pMON8252 encoded glyphosate resistant variant enzyme is 12.6, which is similar to that of the progenitor glycine (101) to alanine variant whose ratio is 10.0. However, the pMON8252 enzyme has a K$_m$ for PEP that is four fold lower than the glycine (101) to alanine variant. The lowering of the K$_m$ for PEP makes the pMON8252 variant enzyme more efficient kinetically, as demonstrated by its ability to support the growth of E. coli even when expressed with the weak promoter of the vector in MOPS medium containing high concentrations of glyphosate. This demonstrated that the selection system allowed for the induction and identification of mutations of the petunia EPSPS glycine (101) to alanine variant enzyme which would maintain the glyphosate resistant properties of the original variant, but lower the K$_m$ for PEP. The pMON8252 results also demonstrated that the improvements in the K$_m$ for PEP could be selected in the heterologous bacterial expression system described above.

H) Identification of the pMON8252 Mutation.

To identify the NG induced amino acid changes responsible for the improved glyphosate resistant properties of the pMON8252 variant EPSP synthase enzyme, the DNA sequence of the entire coding sequence region was determined. The pMON8252 plasmid DNA was sequenced directly by the dideoxy DNA sequencing method of Sanger using the double strand plasmid DNA as a template. Five synthetic DNA oligonucleotides homologous to the petunia EPSPS sequence were used to sequence the entire coding sequence region in one contiguous sequence. The synthetic DNA oligonucleotide primers were 17 nucleotides in length and were spaced approximately 300 bp apart from each other. Approximately 300 ng of double strand pMON8252 plasmid DNA was used for each sequencing reaction. Double strand plasmid DNA, in a 20 μl volume, was denatured by the addition of 2 μl of a 2M NaOH/2 mM EDTA solution and incubating 5 minutes at room temperature followed by neutralization with the addition of 3 μl of 3M sodium acetate, pH 4.8. The volume was diluted to 32 μl by the addition of 7 μl water. The denatured plasmid DNA was precipitated by the addition of 75 μl ethanol and freezing 5 minutes on dry ice, followed by centrifugation for 10 minutes at 5° C. in a microfuge. The DNA pellets were dissolved in 7 μl of water. Synthetic oligonucleotide primer DNA (5 ng) was annealed to denatured plasmid DNA and sequenced using the reagents and protocol from a commercially available DNA sequencing kit from United States Biochemical Corporation. The presence of the glycine (101) to alanine substitution was confirmed in the DNA sequence. In addition, there was a single guanine to adenine transition at the first nucleotide position of the GCT codon for alanine 192 in the mature petunia EPSP synthase, resulting in an alanine to threonine amino acid substitution at the 192 position. The guanine to adenine transition is consistent with the type of mutation known to be induced by NG. An additional point mutation was observed, but the amino acid was conserved. The point mutation was a guanine to adenine transition in the third position of the GAG codon for glutamic acid at amino acid position 4. The resulting codon, GAA also codes for glutamic acid. Thus, the improved kinetic properties of the pMON8252 encoded glyphosate resistant petunia EPSPS variant enzyme are due to a combination of two substitutions: one resulting in the glycine (101) to alanine change, the other resulting in an alanine (192) to threonine amino acid change.

The petunia EPSP synthase coding sequence containing the glycine (101) to alanine and alanine (192) to threonine substitutions was engineered for appropriate expression in plant cells. Construction of the intermediate plant transformation vector and *Agrobacterium tumefaciens*-based transformations of plant cells is described below.

Construction of pMON10079

Figure 3:
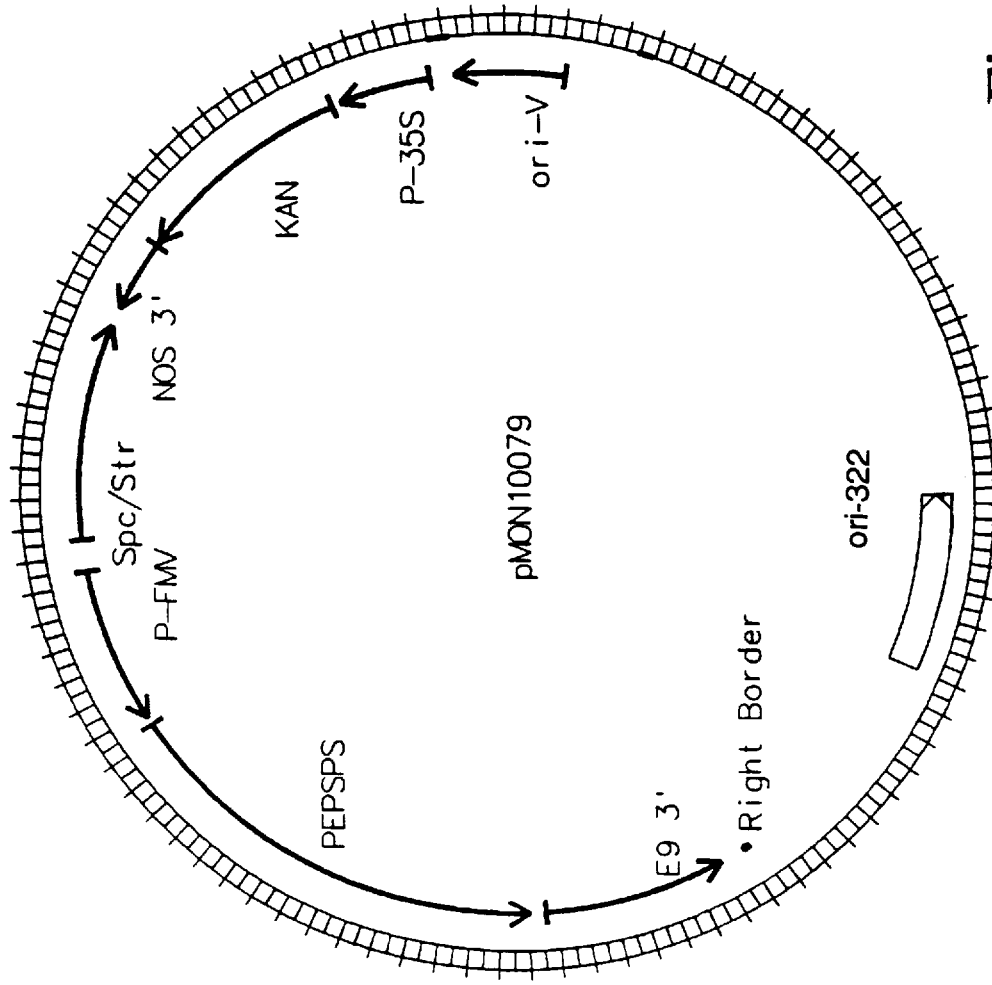
FIG. 3 represents a map of plasmid pMON10079.

The pMON10079 plasmid, a map of which is shown in FIG. 3, contains the following DNA segments. A 0.93 kb fragment isolated from transposon Tn7 which encodes bacterial spectinomycin/streptomycin resistance (Spc/Str) and is a determinant for selection in *E. coli* and *Agrobacterium tumefaciens* (Fling et al. 1985). This is joined to the chimeric kanamycin resistance gene engineered for plant expression to allow selection of the transformed tissue. The chimeric gene consists of the 0.35 kb cauliflower mosaic virus 35S promoter (P-35S) (Odell et al. 1985), the 0.83 kb neomycin phosphotransferase typeII gene (KAN), and the 0.26 kb 3'-nontranslated region of the nopaline synthase gene (NOS 3') (Fraley et al. 1983). The next segment is the 0.75 kb origin of replication from the RK2 plasmid (ori-V) (Stalker et al. 1981). It is joined to the 3.1 kb SalI to PvuI segment of pBR322 which provides the origin of replication for maintenance in *E. coli* (ori-322), and the bom site for the conjugational transfer into the *Agrobacterium tumefaciens* cells. Next is the 0.36 kb PvuI to BclI fragment from the pTiT37 plasmid which contains the nopaline-type T-DNA right border region (Fraley et al. 1985). The last segment is the chimeric gene engineered to overproduce the 5-enolpyruvylshikimate-3-phosphate synthase enzyme (EPSPS) in plants (Shah et al. 1986). The chimeric gene consists of the 0.6 kb 35S promoter from the figwort mosaic virus (P-FMV) (Gowda et al. 1989), the 1.6 kb *Petunia hybrida* EPSPS with two amino acid changes (gly-ala, ala-thr), and the 0.7 kb 3' nontranslated region of the pea rbcS-E9 gene (E9 3') (Coruzzi et al. 1984, and Morelli et al. 1985).

The pMON10079 vector was mobilized into the ABI *Agrobacterium tumefaciens* strain A208 carrying the disarmed Ti plasmid pTiC58 (Koncz and Schell 1986). The Ti plasmid does not carry the T-DNA phytohormone genes, and the strain is therefore unable to cause the crown gall disease. Mating of pMON10079 into ABI was performed by the triparental conjugation system using the helper plasmid pRK2013 (Ditta et al. 1980). When the plant tissue is incubated with the ABI::pMON10079 conjugate, the vector is transferred to the plant cells by the vir functions encoded by the disarmed pTiC58 plasmid. The vector opens at the T-DNA right border region, and the entire pMON10079 vector sequence is inserted into the host plant chromosome. The pTiC58 Ti plasmid does not transfer to the plant cells but remains in the *Agrobacterium*.

Tobacco plants transformed with the pMON10079 vector exhibit resistance to glyphosate. Eleven plants were transformed and all eleven exhibited glyphosate resistance when crude extracts of the plant's EPSPS were assayed in the presence of 1.0 mM glyphosate. Thus, the petunia EPSPS variant with the glycine to alanine substitution at position 101 and the alanine to threonine substitution at position 192 does confer glyphosate tolerance to transformed plants.

The variant ESPS synthase polypeptides and EPSPS genes of the present invention may be prepared by either polypeptide synthesis or isolation and mutagenesis of an EPSP synthase gene to produce the above described glyphosate-tolerant molecule. Since it is foreseen that the greatest utility of the present invention is in the preparation of glyphosate-tolerant plants, nucleotide sequences (either cDNA or genomic) encoding the glyphosate-tolerant EPSP synthase can be easily prepared in the following manner.

cDNA Coding Sequences

Total RNA is isolated from the source material which includes, but is not necessarily limited to, fungi and plant tissue. PolyA-mRNA is selected by oligodT cellulose chromatography. A cDNA library is then prepared using the polyA-mRNA. The cDNA library is then screened using a previously cloned EPSP synthase sequence or a suitable oligonucleotide probe. Suitable oligonucleotide probes include probes based on the conserved region having the amino acid sequence (L-G-N-A-G-T-A) or probes based on the amino acid sequence of other portions of the EPSP synthase molecule. The cDNA fragments selected by hybridization are then sequenced to confirm that the fragment encodes the EPSP synthase and to determine the DNA sequence encoding and adjacent to the conserved amino acid sequence described above.

The EPSP synthase clone is then altered by oligonucleotide mutagenesis to insert the DNA substitution necessary to result in the alanine for glycine substitution in the first conserved amino acid sequence and a threonine for alanine substitution in a second conserved amino acid sequence as previously described. The above procedure produces a cDNA sequence which encodes the glyphosate-tolerant EPSP synthase of the present invention based on the wild-type EPSP synthase of the selected source material. This structural coding sequence can be inserted into functional chimeric gene constructs and inserted into suitable plant transformation vectors to be used in preparing transformed plant cells and regenerated plants using the methodology described herein.

Genomic EPSP Synthase Clone

Generally it is preferred that the plant tissue from the plant species to be transformed also serve as the source material for the DNA coding sequence for the glyphosate-tolerant EPSP synthase of the present invention. In this way, one would easily obtain the chloroplast transit peptide coding sequence from the plant species to be transformed. In some cases, it may be beneficial to utilize a genomic clone from the plant species which comprises the introns normally found in the endogenous EPSP synthase gene. The general method described above is also applicable with the exception that the probes are used to screen a genomic DNA library constructed from the selected plant tissue. Detailed examples better elucidating this preparation of cDNA and genomic DNA glyphosate-tolerant EPSP synthase constructs of the present invention are provided below.

PREPARATION OF EPSP SYNTHASE PLANT TRANSFORMATION VECTORS

I. cDNA Encoding the EPSP Synthase of Petunia

Described below is the methodology employed to prepare the cDNA clone of petunia EPSP synthase which was used in the mutagenesis procedure described above. Clones of wild-type EPSP synthases from other plant sources can be obtained in a similar manner and the above described mutations introduced by site directed mutagenesis.

A. Creation of MP4-G Cell Line

The starting cell line, designated as the MP4 line, was derived from a Mitchell diploid petunia (see e.g., Ausubel 1980). The MP4 cells were suspended in Murashige and Skoog (MS) culture media, (GIBCO, Grand Island, N.Y.) All transfers involved dispensing 10 ml of suspension cultures into 50 ml of fresh media. Cultivation periods until the next transfer ranged from 10 to 14 days, and were based on visual indications that the culture was approaching saturation.

Approximately 10 ml of saturated suspension culture (containing about 5×10$^6$ cells) were transferred into 50 ml of MS media containing 0.5 mM glyphosate. The sodium salt of glyphosate was used throughout the experiments described herein. The large majority of cells were unable to reproduce in the presence of the glyphosate. The cells which survived (estimated to be less than 1% of the starting population) were cultured in 0.5 mM glyphosate and transferred to fresh media containing glyphosate every 10 to 14 days.

After two transfers, the surviving cells were transferred into fresh media containing 1.0 mM glyphosate. After two transfers at 1.0 mM, the surviving cells were transferred sequentially into 2.5 mM glyphosate, 5.0 mM glyphosate, and 10 mM glyphosate.

The MP4-G cells prepared as described above were subsequently shown by a Southern blot analysis (Southern, 1975) to have about 15–20 copies of the EPSP synthase gene, due to a genetic process called "gene amplification" (see e.g. Schimke 1982). Although spontaneous mutations might have occurred during the replication of any cell, there is no indication that any mutation or other modification of the EPSP synthase gene occurred during the gene amplification process. The only known difference between the MP4 and the MP4-G cells is that the MP4-G cells contain multiple copies of an EPSP synthase gene and possibly other genes located near it on the chromosomes of the cells.

B. Purification and Sequencing of EPSP Synthase Enzymes

Petunia cells from the MP4-G cell line were harvested by vacuum filtration, frozen under liquid N$_2$, and ground to a powder in a Waring blender. The powder was suspended in 0.2M Tris-HCl, pH 7.8, containing 1 mM EDTA and 7.5% w/v polyvinylpolypyrrolidone. The suspension was centrifuged at about 20,000×gravity for 10 minutes to remove cell debris. Nucleic acids were precipitated from the supernatant by addition of 0.1 volume of 1.4% protamine sulfate and discarded.

The crude protein suspension was purified by five sequential steps (see Mousdale & Coggins 1984 and Steinrucken & Amrhein 1985) which involved: (1) ammonium sulfate precipitation; (2) diethylaminoethyl cellulose ion exchange chromatography; (3) hydroxyapatite chromatography; (4) hydrophobic chromatography on a phenylagarose gel; and (5) sizing on a Sephacryl S-200 gel.

The purified EPSP synthase polypeptide was degraded into a series of individual amino acids by Edman degradation by a Model 470A Protein Sequencer (Applied Biosystems Inc., Foster City, Calif.), using the methods described in Hunkapiller 1983a. Each amino acid derivative was analyzed by reverse phase high performance liquid chromatography, as described by Hunkapiller 1983b, using a cyanopropyl column with over 22,000 theoretical plates (IBM Instruments, Wallingford Conn.). A partial amino acid sequence for petunia EPSP synthase is shown in Table 1.

TABLE 1

Petunia EPSP Synthase Sequences

|  | 8 | 9 | 10 | 11 | 12 | 13 |
|---|---|---|---|---|---|---|
| Amino Acid: | Gly | Pro | Ile | Lys | Glu | Ile |
| mRNA strand: | 5'CAP | CCN | AUU C A | GAP | CAP | AUU C A |
| Complementary DNA strand: | 3-GTQ | GGN | TAA G U | TTQ | CTQ | TAA G U |
| Synthetic DNA Probes: |  |  |  |  |  |  |
| EPSP1: | 3'-GTQ | GGP | TAP | TTQ | CTQ | TA |
| EPSP2: | 3'-GTQ | GGQ | TAP | TTQ | CTQ | TA |
| EPSP3: | 3'-GTQ | GGN | TAT | TTQ | CTQ | TA |
| Exact mRNA Sequence: | 5'-CAA | CCC | AUU | AAA | GAG | AUU |

C. Synthesis of Probes

Using the genetic code, the amino acid sequence indicated in Table 1 was used to determine the possible DNA codons which are capable of coding for each indicated amino acid. Using this information, three different probe mixtures were created and designated as EPSP-1, EPSP-2, and EPSP-3, as shown in Table 1. In this table, A, T, U, C, and G represent the nucleotide bases: adenine, thymine, uracil, cytosine and guanine. The letters P, Q, and N are variables; N represents any of the bases; P represents purines (A or G); Q represents pyrimidines (U, T, or C). All oligonucleotides were synthesized by the method of Adams (1983). Whenever an indeterminate nucleotide position (P, Q or N) was reached, a mixture of appropriate nucleotides was added to the reaction mixture. Probes were labeled 20 pmol at a time shortly before use with 100 μci γ-[$^{32}$P]-ATP (Amersham) and 10 units polynucleotide kinase in 50 mM Tris-HCl, pH 7.5; 10 mM MgCl$_2$, 5 mM DTT, 0.1 mM EDTA, and 0.1 mM spermidine. After incubation for 1 hour at 37° C., the probes were repurified on either a 20% acrylamide, 8M urea gel or by passage over a 5 ml column of Sephadex G25 in 0.1M NaCl, 10 mM Tris-HCl, pH 7.5, 1 mM EDTA.

D. Preparation of mRNA and Preliminary Testing of Probes (a) Poly-A mRNA

Total RNA was isolated from the MP4 (glyphosate sensitive) and MP4-G (glyphosate resistant) cell lines as described by Goldberg (1981). Total RNA was further sedimented through a CsCl cushion as described by Depicker (1982). Poly-A mRNA was selected by oligo-dT cellulose chromatography. The yield of poly-A RNA was 1.1 micrograms (μg) per gram of MP4 cells and 2.5 μg/gm of MP4-G cells.

(b) Gel Processing of RNA

Ten μg of poly-A RNA from the MP4 or MP4-G cell lines were precipitated with ethanol and resuspended in 1× MOPS buffer (20 mM MOPS, pH 7.0, 5 mM sodium acetate and 1 mM EDTA, pH 8.0) containing 50% formamide and 2.2M formaldehyde. RNA was denatured by heating at 65° C. for 10 minutes. One-fifth volume of a loading buffer containing 50% glycerol, 1 mM EDTA, 0.4% bromophenol blue and 0.4% xylene cyanol was then added. RNA was fractionated on a 1.3% agarose gel containing 1.1M formaldehyde until bromophenol blue was near the bottom. HaeIII-digested φX174 DNA, labelled with $^{32}$P, was run as a size standard. The DNA markers indicated approximate sizes for the RNA bands.

(c) Transfer of RNA to Nitrocellulose

RNA was transferred to nitrocellulose (#BA85, Schleicher & Schuell, Keene, N.H.) by blotting the gels overnight using 20× SSC (1× SSC is 0.15M NaCl, 0.015M sodium citrate, pH 7.0) as the transfer buffer. After transfer, filters were air-dried and baked in a vacuum oven for 2–3 hours at 80° C.

(d) Preliminary Hybridization with Radioactive Probes

Filters were prehybridized in 6× SSC, 1× Denhardt's solution (1× Denhardt's solution is 0.02% Ficoll, 0.02% polyvinylpyrrolidone, 0.02% bovine serum albumin), 0.5% NP-40, and 200 μg/ml *E. coli* transfer RNA at 50° C. for 4 hours. Hybridization was carried out in a similar fresh solution containing 2×10⁶ cpm/ml of either EPSP-1 or EPSP-2 probe for 48 hours at 32° C. The EPSP-3 probe was not tested since it contained a codon (ATA) that is rarely found in the petunia genome. Hybridization temperature (32° C.) used in each case was 10° C. below the dissociation temperature (Td) calculated for the oligonucleotide with the lowest GC content in a mixture. The Td of the probe was approximated by the formula 20° C.×(A+T)+4° C.×(G+C).

(e) Filter Washing

The filters were washed twice for 15–20 minutes at room temperature in 6× SSC and then for 5 minutes at 37° C. with gentle shaking. Filters were then wrapped in plastic film and autoradiographed for 12–14 hours at −70° C. with two intensifying screens. The filters were then washed again for 5 minutes with gentle shaking at a temperature of 42° C. The filters were autoradio-graphed again for 12–14 hours. The autoradiographs indicated that the probe EPSP-1 hybridized to an RNA of approximately 1.9 kb in the lane containing the poly-A RNA from the MP4-G cell line. No hybridization to this RNA was detected in the lane containing the poly-A RNA from the MP4 cell line. This result was attributed to overproduction of EPSP synthase mRNA by the MP4-G cell line. The probe EPSP-2, which differs from EPSP-1 by a single nucleotide, showed barely detectable hybridization to the 1.9 kb mRNA of the MP4-G cell line but hybridized strongly to a 1.0 kb mRNA from both cell lines. However, the 1.0 kb DNA was not sufficient to encode a polypeptide of 50,000 daltons, and it is believed that one of the sequences in the EPSP-2 probe hybridized to an entirely different sequence in the library. These results suggested that degenerate probe mixture EPSP-1 contained the correct sequence for EPSP synthase. This mixture was used in all subsequent degenerate probe hybridization experiments.

E. Preparation of λgt10 cDNA library (a) Materials Used

AMV reverse transcriptase was purchased from Seikagaku America, Inc., St. Petersburg, Fla.; the large fragment of DNA polymerase I (Klenow polymerase) was from New England Nuclear, Boston, Mass.; S1 nuclease and tRNA were from Sigma; AcA 34 column bed resin was from LKB, Gaithersburg, Md.; EcoRI, EcoRI methylase and EcoRI linkers were from New England Biolabs, Beverly Mass.; RNAsin (ribonuclease inhibitor) was from Promega Biotech, Madison, Wis. and all radioactive compounds were from Amersham, Arlington Hts., Ill.

The λgt10 vector (ATCC No. 40179) and associated *E. coli* cell lines were supplied by Thanh Huynh and Ronald Davis at Stanford University Medical School (see Huynh 1985). This vector has three important characteristics: (1) it has a unique EcoRI insertion site, which avoids the need to remove a center portion of DNA from the phage DNA before inserting new DNA; (2) DNA ranging in size from zero to about 8,000 bases can be cloned using this vector; and, (3) a library can be processed using *E. coli* MA150 cells (ATCC No. 53104) to remove clones which do not have DNA inserts.

(b) cDNA First Strand Synthesis

Poly-A mRNA was prepared as described in section D. (a) above, and resuspended in 50 mM Tris (pH 8.5), 10 mM MgCl$_2$, 4 mM DTT, 40 mM KCl, 500 μM of d(AGCT)TP, 10 μg/ml dT$_{12-18}$ primer, and 27.5 units/ml RNAsin. In a 120 μl reaction volume, 70 units reverse transcriptase were added per 5 μg of poly-A RNA. One reaction tube contained γ-$^{32}$P-dCTP (5 μCi/120 μl reaction) to allow monitoring of cDNA size and yield and to provide a first strand label to monitor later reactions. In order to disrupt mRNA secondary structure, mRNA in H$_2$O was incubated at 70° C. for 3 minutes and the tube was chilled on ice. Reverse transcriptase was added and the cDNA synthesis was carried out at 42° C. for 60 minutes. The reaction was terminated by the addition of EDTA to 50 mM. cDNA yield was monitored by TCA precipitations of samples removed at the start of the reaction and after 60 minutes. Following cDNA synthesis, the cDNA existed as a cDNA-RNA hybrid. The cDNA-RNA hybrid was denatured by heating the mixture in a boiling water bath for 1.5 minutes, and cooled on ice.

(c) Second Strand DNA Synthesis

Single-stranded cDNA was allowed to selfprime for second strand synthesis. Both Klenow polymerase and reverse transcriptase were used to convert ss cDNA to ds cDNA. Klenow polymerase is employed first since its 3'–5' exonuclease repair function is believed to be able to digest non-flush DNA ends generated by self-priming and can then extend these flush ends with its polymerase activity. Reverse transcriptase is used in addition to Klenow polymerase, because reverse transcriptase is believed to be less likely to stop prematurely once it has bound to a template strand. The Klenow polymerase reaction was in a final 100 μl volume excluding enzyme. The reaction mix included 50 mM HEPES, pH 6.9, 10 mM MgCl$_2$, 50 mM KCl, 500 μM of each dNTP and cDNA. To begin the reaction, 20 to 40 units of Klenow polymerase (usually less than 5 μl) were added and the tubes incubated at 15° C. for 5 hours. The reaction was terminated by the addition of EDTA to 50 mM. The mix was extracted with phenol and the nucleic acids were precipitated, centrifuged and dried.

The reverse transcriptase reaction to further extend the anti-complementary DNA strand was performed as described for the reaction to originally synthesize cDNA, except dT$_{10-18}$ primer and RNAsin were absent, and 32 units of reverse transcriptase were used in a 120 μl reaction. The reaction was terminated by the addition of EDTA to 50 mM. The mixture was extracted with an equal volume of phenol and the nucleic acid was precipitated, centrifuged and dried.

(d) S1 Nuclease Treatment

200 μl of 2× S1 buffer (1× S1 buffer is 30 mM sodium acetate, pH 4.4, 250 mM NaCl, 1 mM ZnCl$_2$), 175 μl of H$_2$O and 525 units of S1 nuclease were added to the tubes containing 125 μl of the second strand synthesis reaction product. The tubes were incubated at 37° C. for 30 minutes and the reaction was terminated by addition of EDTA to 50 mM. The mixture was extracted with an equal volume of phenol/chloroform (1:1). The aqueous phase was extracted with ethyl ether to remove residual phenol. The DNA was precipitated with ethanol and air dried.

(e) EcoRI Methylation Reaction

Since the ds cDNAs were copied from a large variety of mRNAs, many of the ds cDNAs probably contained internal EcoRI restriction sites. It was desired to protect such cleavage sites from EcoRI cleavage, to enable the use of blunt-ended EcoRI linkers which were subsequently cleaved with EcoRI to create cohesive overhangs at the termini.

In an effort to prevent the undesired cleavage of internal EcoRI sites, the ds cDNA was methylated using EcoRI methylase. DNA pellets were dissolved in 40 μl of 50 mM Tris pH 7.5, 1 mM EDTA, 5 mM DTT. Four μl of 100 μM S-adenosyl-L-methionine and 1 μl (80 units) of EcoRI methylase were added. Tubes were incubated at 37° C. for 15 minutes and then at 70° C. for 10 minutes to inactivate the methylase.

It was subsequently discovered that the methylation reaction described above was unsuccessful in preventing EcoRI cleavage at an internal site within the EPSP synthase coding region, apparently because of inactive methylase reagent. The cleavage of the internal EcoRI site required additional steps to isolate a full-length cDNA, as described below. To avoid those additional steps, the methylation reagents and reaction conditions should be used simultaneously on the cDNA and on control fragments of DNA, and protection of the control fragments should be confirmed by EcoRI digestion before digestion is performed on the cDNA.

(f) DNA Polymerase I Fill-In Reaction

To the tube containing 45 μl of cDNA (prepared as described above) were added 5 μl of 0.1M $MgCl_2$, 5 μl of 0.2 mM d(ACGT)TP and 10 units of DNA polymerase I. The tube was incubated at room temperature for 10 minutes. The reaction was terminated by the addition of EDTA to 25 mM. One microgram of uncut λgt10 DNA was added as a carrier and the mix was extracted with phenol/chloroform (1:1). The nucleic acid in the mix was precipitated with ethanol, centrifuged and dried.

(g) Ligation of EcoRI Linkers to Methylated ds cDNA

Approximately 400 pmoles of EcoRI linkers (5'-CGGAATTCCG-3') were dissolved in 9 μl of 20 mM Tris, pH 8.0, 10 mM $MgCl_2$, 10 mM DTT containing 50 μCi of γ-$^{32}$P-ATP (5000 Ci/mmole) and 2 units of T4 polynucleotide kinase. The oligonucleotides were incubated at 37° C. for 30 minutes to allow them to anneal to each other, creating double-stranded, blunt-ended linkers. Two units of T4 polynucleotide kinase and 1 μof 10 mM ATP were added and incubated at 37° C. for an additional 30 minutes. The linkers were stored at -20° C. The methylated DNA pellet was resuspended in tubes containing 400 pmoles of the kinased linkers. Ligation of the EcoRI linkers to the methylated DNA was carried out by adding 1 μl of T4 ligase and incubating the reaction mixture at 12°–14° C. for 2 days.

(h) Digestion with EcoRI to Create Cohesive Termini To 11 μl of the reaction product from Section 1.E.(g) above, 10 μl of a solution containing 50 mM Tris, pH 7.5, 10 mM $MgSO_4$, 200 mM NaCl were added. T4 DNA ligase was heat inactivated by incubation at 70° C. for 10 minutes. Forty units of EcoRI were added and the incubation was carried out at 37° C. for 3 hours. The reaction was terminated by addition of 50 mM. The sample was clarified by centrifugation and applied to an AcA 34 column.

(i) AcA 34 Column Chromatography

Free linkers (those not ligated) were removed from ds cDNA with attached linkers, to prevent them from interfering with the insertion of the desired ds cDNAs into the cloning vectors. AcA 34 resin (a mixture of acrylamide and agarose beads, normally used for sizing) preswollen in 2 mM citrate buffer and 0.04% sodium azide in water, was added to the 1 ml mark of a 1 ml plastic syringe plugged with glass wool. The column was equilibrated with 10 mM Tris-HCl pH 7.5, 1 mM EDTA, 400 mM NaCl. The ds cDNA mixtures with ligated linkers and free linkers (~45 μl) was brought to 400 mM NaCl. 1 μl of 0.5% bromophenol blue dye (BPB) was added, and the sample was applied to the column which was run in equilibration buffer at room temperature. Ten 200 μl fractions were collected. The BPB dye normally eluted from the column in the sixth tube or later. Tubes 1 and 2 were combined and used as the source of ds cDNA for cloning.

(j) Assembly of λgt10 clones

The ds cDNA was mixed with 1 μg of EcoRI-cut λgt10 DNA, precipitated with ethanol, and centrifuged. After washing the pellet once with 70% ethanol, the DNA pellet was air dried and resuspended in 4.5 μl of 10 mM Tris-HCl pH 7.5, 10 mM $MgCl_2$, 50 mM NaCl. To anneal and ligate the cDNA inserts to the left and right arms of the λgt10 DNA, the mixture was heated at 70° C. for 3 minutes, then at 50° C. for 15 minutes. The mixture was chilled on ice and 0.5 μl each of 10 mM ATP, 0.1M DTT, and sufficient T4 DNA ligase to ensure at least 90% completion were added. The reaction was incubated at 14° C. overnight, which allowed the insertion of the ds cDNA into the EcoRI site of the λgt10 DNA. The resulting DNA was packaged into phage particles in vitro using the method described by Scherer 1981.

(k) Removal of Phages Without Inserts

Insertion of a cDNA into the EcoRI site of λgt10 results in inactivation of the C1 gene. λgt10 phages with inactivated C1 genes (i.e., with inserts) replicate normally in E. coli MA150 cells. By contrast, λgt10 phages without inserts are unable to replicate in the MA150 strain of E. coli. This provides a method of removing λgt10 clones which do not have inserts.

The phages in the library were first replicated in E. coli C600 (M+R-) cells which modified the λgt10 DNA to protect it from the E. coli MA150 restriction system. A relatively small number of E. coli C600 cells were infected and then plated with a 20 fold excess of MA150 (M+R+) cells. The primary infection thus occurred in the M+R–cells where all the phages will grow, but successive rounds of replication occurred in the MA150 cells which prevented the replication of phages without inserts. The amplified phage library was collected from the plates, and after removal of agar and other contaminants by centrifugation, the recombinant phages were ready to use in screening experiments.

F. Screening of cDNA Library: Selection of PMON9531

Approximately 600 phages (each plate) were spread on 10 cm×10 cm square plates of solid NZY agar (Maniatis 1982) with 0.7% agarose. A translucent lawn of E. coli MA150 cells were growing on the plates. Areas where the phages infected and killed the E. coli cells were indicated by clear areas called "plaques," which were visible against the lawn of bacteria after an overnight incubation of the plates at 37° C. Six plates were prepared in this manner. The plaques were pressed against pre-cut nitrocellulose filters for about 30 minutes. This formed a symmetrical replica of the plaques. To affix the phage DNA, the filters were treated with 0.5M NaOH and 2.5M NaCl for 5 minutes. The filters were then treated sequentially with 1.0M Tris-HCl, pH 7.5 and 0.5M Tris-HCl, pH 7.5 containing 2.5M NaCl to neutralize the NaOH. They were then soaked in chloroform to remove bacterial debris. They were then air-dried and baked under a vacuum at 80° C. for 2 hours, and allowed to cool to room temperature. The filters were then hybridized with $^{32}$P-labelled EPSP-1 probe (2×$10^6$ cpm/filter) as described in Section 1.D(e) above. After 48 hours of hybridization, the filters were washed in 6× SSC at room temperature twice for 20 minutes and then at 37° C. for 5 minutes. These washes removed non-specifically bound probe molecules, while probe molecules with the exact corresponding sequence (which was unknown at the time) remained bound to the phage DNA on the filter. The filters were analyzed by autoradiography after the final wash. After the first screening step, seven positively hybridizing signals appeared as black spots on the autoradiograms. These plaques were removed from the plates and replated on fresh plates at a density of 100–200 plaques/plate. These plates were screened using the procedure described above. Four positively hybridizing phages were selected. DNA was isolated from each of these four clones and digested with EcoRI to determine the sizes of the cDNA inserts. The clone containing the largest cDNA insert, approximately 330 bp, was selected, and designated λE3. The cDNA insert from λE3 was inserted into plasmid pUC9 (Vieira 1981), and the resulting plasmid was designated pMON9531.

To provide confirmation that the pMON9531 clone contained the desired EPSP synthase sequence, the insert was removed from the pMON9531 clone by digestion with EcoRI. This DNA fragment was then sequenced by the chemical degradation method of Maxam (1977). The amino acid sequence deduced from the nucleotide sequence corresponded to the EPSP synthase partial amino acid sequence shown in Table 1.

G. Creation of λF7 Genomic DNA Clone

In order to obtain the entire EPSP synthase gene, chromosomal DNA from the MP4-G cells line was digested with BamHI and cloned into a phage vector to create a library, which was screened using the partial EPSP synthase sequence from pMON9531 as a probe.

(a) Preparation of MP4-G Chromosomal DNA Fragments

MP4-G cells were frozen and pulverized in a mortar with crushed glass in the presence of liquid nitrogen. The powdered cells were mixed with 8 ml/g of cold lysis buffer containing 8.0M urea, 0.35M NaCl, 0.05M Tris-HCl (pH 7.5), 0.02M EDTA, 2% sarkosyl and 5% phenol. The mixture was stirred with a glass rod to break up large clumps. An equal volume of a 3:1 mixture of phenol and chloroform containing 5% isoamyl alcohol was added. Sodium dodecyl sulfate (SDS) was added to a final concentration of 0.5%. The mixture was swirled on a rotating platform for 10–15 minutes at room temperature. The phases were separated by centrifugation at 6,000×g for 15 minutes. The phenol/chloroform extraction was repeated. Sodium acetate was added to the aqueous phase to a final concentration of 0.15M and the DNA was precipitated with ethanol. The DNA was collected by centrifugation, dissolved in 1× TE (10 mM Tris-HCl, pH 8.0, 1 mM EDTA) and banded in a CsCl-ethidium bromide gradient. The DNA was collected by puncturing the side of the tube with a 16 gauge needle. The ethidium bromide was extracted with CsCl-saturated isopropanol, and the DNA was dialyzed extensively against 1× TE. Approximately 400 μg of DNA was isolated from 12 g of cells.

MP4-G chromosomal DNA (10 μg) was digested to completion with 30 units of BamHI in a buffer containing 10 mM Tris, pH 7.8, 1 mM DTT, 10 mM MgCl$_2$, 50 mM NaCl for 2 hours at 37° C. The DNA was extracted with phenol followed by extraction with chloroform and precipitated with ethanol. The DNA fragments were suspended in 1× TE at a concentration of 0.5 μg/ul.

(b) Cloning of MP4-G Chromosomal DNA Fragments in λMG14

DNA from phage λMG14 (obtained from Dr. Maynard Olson of the Washington University School of Medicine, St. Louis, Mo.) was prepared by the method described in Maniatis 1982. 150 μg of DNA was digested to completion with BamHI in a buffer containing 10 mM Tris-HCl, pH 7.8, 1 mM DTT, 10 mM MgCl$_2$, 50 mM NaCl. The completion of the digest was checked by electrophoresis through 0.5% agarose gel. The phage DNA was then extracted twice with phenol-chloroform-isoamyl alcohol (25:24:1) and precipitated with ethanol. The DNA was resuspended in 1× TE at a concentration of 150 μg/ml. MgCl$_2$ was added to 10 mM and incubated at 42° C. for 1 hour to allow the cohesive ends of λDNA to reanneal. Annealing was checked by agarose gel electrophoresis.

After annealing, DNA was layered over a 38 ml (10–40%, w/v) sucrose gradient in a Beckman SW27 ultracentrifuge tube. The gradient solutions were prepared in a buffer containing 1M NaCl, 20 mM Tris-HCl (pH 8.0), 5 mM EDTA. Seventy-five tig of DNA was loaded onto each gradient. The samples were centrifuged at 26,000 rpm for 24 hours at 15° C. in a Beckman SW 27 rotor. Fractions (0.5 ml) were collected from the top of the centrifuge tube and analyzed for the presence of DNA by gel electrophoresis. The fractions containing the annealed left and right arms of λDNA were pooled together, dialyzed against TE and ethanol-precipitated. The precipitate was washed with 70% ethanol and dried. The DNA was dissolved in TE at a concentration of 500 μg/ml.

The purified arms of the vector DNA and the BamHI fragments of MP4-G DNA were mixed at a molar ratio of 4:1 and 2:1 and ligated using T4 DNA ligase in a ligase buffer containing 66 mM Tris-HCl, pH 7.5, 5 mM MgCl$_2$, 5 mM DTT and 1 mM ATP. Ligations were carried out overnight at 15° C. Ligation was checked by agarose gel eletrophoresis. Ligated phage DNA carrying inserts of MP4-G DNA were packaged into phage capsids in vitro using commercially available packaging extracts (Promega Biotech, Madison, Wis.). The packaged phage were plated in 10 cm×10 cm square plates of NZY agar in 0.7% agarose at a density of approximately 6000 plaques per plate using *E. coli* C600 cells. After overnight incubation at 37° C., the plaques had formed, and the plates were removed from the incubator and chilled at 4° C. for at least an hour. The agar plates were pressed against nitrocellulose filters for 30 minutes to transfer phages to the filters, and the phage DNA was affixed to the filters as described previously. Each filter was hybridized for 40 hours at 42° C. with approximately 1.0×10$^6$ cpm/filter of the 330 bp cDNA insert isolated from the pMON9531 clone, which had been nick-translated, using the procedure described by Maniatis (1982). The specific activity of the probe was 2–3×10$^8$ cpm/μg of DNA. Hybridization was carried out in a solution containing 50% formamide, 5× SSC, 5× Denhardt's solution, 200 μg/ml tRNA and 0.1% SDS. Filters were washed in 1× SSC, 0.2% SDS at 50° C. and autoradiographed. Several positive signals were observed and matched with plaques on the corresponding plate. The selected plaques were isolated from the plates, suspended in SM buffer, and plated with NZY agar. The replica plate screening process was repeated at lower densities until all the plaques on the plates showed positive signals. One isolate was selected for further analysis and was designated as the λF7 phage clone.

H. Preparation of PMON9543 and pMON9556

The DNA from λF7 was digested (separately) with BamHI, BglII, EcoRI, and HindIII. The DNA was hybridized with a nick-translated EPSP synthase sequence from pMON9531 in a Southern blot procedure. Results from that experiment indicated that the complementary sequence from λF7 was on a 4.8 kb BglII fragment. This fragment was inserted into plasmid pUC9 (Vieira 1982), replicated, nick-translated, and used to probe the petunia cDNA library, using hybridization conditions as described in Section 1.(G) and 10$^6$ cpm per filter. A cDNA clone with a sequence that hybridized to the λF7 sequence was identified. The insert of this clone was subcloned into the EcoRI site of pUC9 resulting in pMON9543.

DNA sequence analysis (Maxam 1977) indicated that pMON9543 did not contain the stop codon or the 3' nontranslated region of the EPSP synthase gene. Therefore, the EPSP synthase sequence was removed from pMON9543, nick-translated, and used as a probe to screen the cDNA library again. A clone which hybridized with the EPSP synthase sequence was identified and designated as pMON9556. DNA sequence analysis indicated that the insert in this clone contained the entire 3' region of the EPSP synthase gene, including a polyadenylated tail. The 5' EcoRI end of this insert matched the 3' EcoRI end of the EPSP synthase insert in pMON9531. An entire EPSP synthase coding sequence was created by ligating the EPSP synthase inserts from pMON9531 and pMON9556.

I. Preparation of pMON546 Vector with CaMV35S/EPSP Synthase Gene

The petunia EPSP synthase insert in pMON9531 which contained the 5' portion of the cDNA including the transit peptide and coding sequence through the internal EcoRI site, was modified by site-directed mutagenesis (Zoller et al, 1983) using an M13 vector (Messing 1981 and 1982) to create a BglII site in the 5' non-translated region of the EPSP synthase gene. The modified EPSP synthase sequence was isolated by EcoRI and BglII digestion, and inserted into vector, pMON530, a binary vector for *Agrobacterium*-based plant transformation to obtain pMON536. The 1.62 kb EcoRI—EcoRI fragment which contained the 3' portion of the cDNA from the internal EcoRI site through the 3' untranslated region from pMON9556 was then inserted into pMON536 to obtain pMON546. Since pMON530 already contained a 35S promoter from a cauliflower mosaic virus (CaMV) next to the BglII site, this created a chimeric CaMV35S/EPSP synthase gene containing the wild type coding sequence in pMON546.

pMON530, a derivative of pMON505 carrying the 35S-NOS cassette, was prepared in the following manner:

The CaMV35S promoter was isolated from the pOS-1 clone of CM4–184 as an AluI (n 7143)-EcoRI*(n 7517) fragment which was inserted first into pBR322 cleaved with BamHI, treated with Klenow fragment of DNA polymerase I and then cleaved with EcoRI. The promoter fragment was then excised from pBR322 with BamHI and EcoRI, treated with Klenow polymerase and inserted into the SmaI site of M13mp8 so that the EcoRI site of the mp8 multi-linker was at the 5' end of the promoter fragment. The nucleotide numbers refer to the sequence of CM1841 (Gardner et al., 1981). Site directed mutagenesis was then used to introduce a G at nucleotide 7464 to create a BglII site. The CaMV35S promoter fragment was then excised from the M13 as a 330 bp EcoRI-BglII fragment which contains the CaMV35S promoter, transcription and 30 nucleotides of the 5' non-translated leader but does not contain any of the CaMV translational initiators nor the CaMV35S transcript polyadenylation signal that is located 180 nucleotides downstream from the start of transcription (Covey et al., 1981; Guilley et al., 1982). The CaMV35S promoter fragment was joined to a synthetic multi-linker and the NOS 3' non-translated region and inserted into pMON200 (Fraley et al., 1985; Rogers et al., 1986) to give pMON316 (see Rogers et al., 1987).

Plasmid pMON316 contains unique cleavage sites for BglII, ClaI, KpnI, XhoI and EcoRI located between the 5' leader and the NOS polyadenylation signals. Plasmid pMON316 retains all of the properties of pMON200. The complete sequence of the CaMV35S promoter, multi-linker and NOS 3' segment is given in Rogers et al., 1987. This sequence begins with the XmnI site created by Klenow polymerase treatment to remove the EcoRI site located at the 5' end of the CaMV35S promoter segment.

Plasmid pMON530 (Rogers et al., 1987) is a derivative of pMON505 prepared by transferring the 2.3 kb StuI-HindIII fragment of pMON316 into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 in which the Ti plasmid homology region, LIH, has been replaced with a 3.8 kb HindIII to SmaI segment of the mini RK2 plasmid, pTJS75 (Schmidhauser & Helinski, 1985). This segment contains the RK2 origin of replication, oriV, and the origin of transfer, oriT, for conjugation into *Agrobacterium* using the tri-parental mating procedure (Horsch & Klee, 1986).

Figure 4:
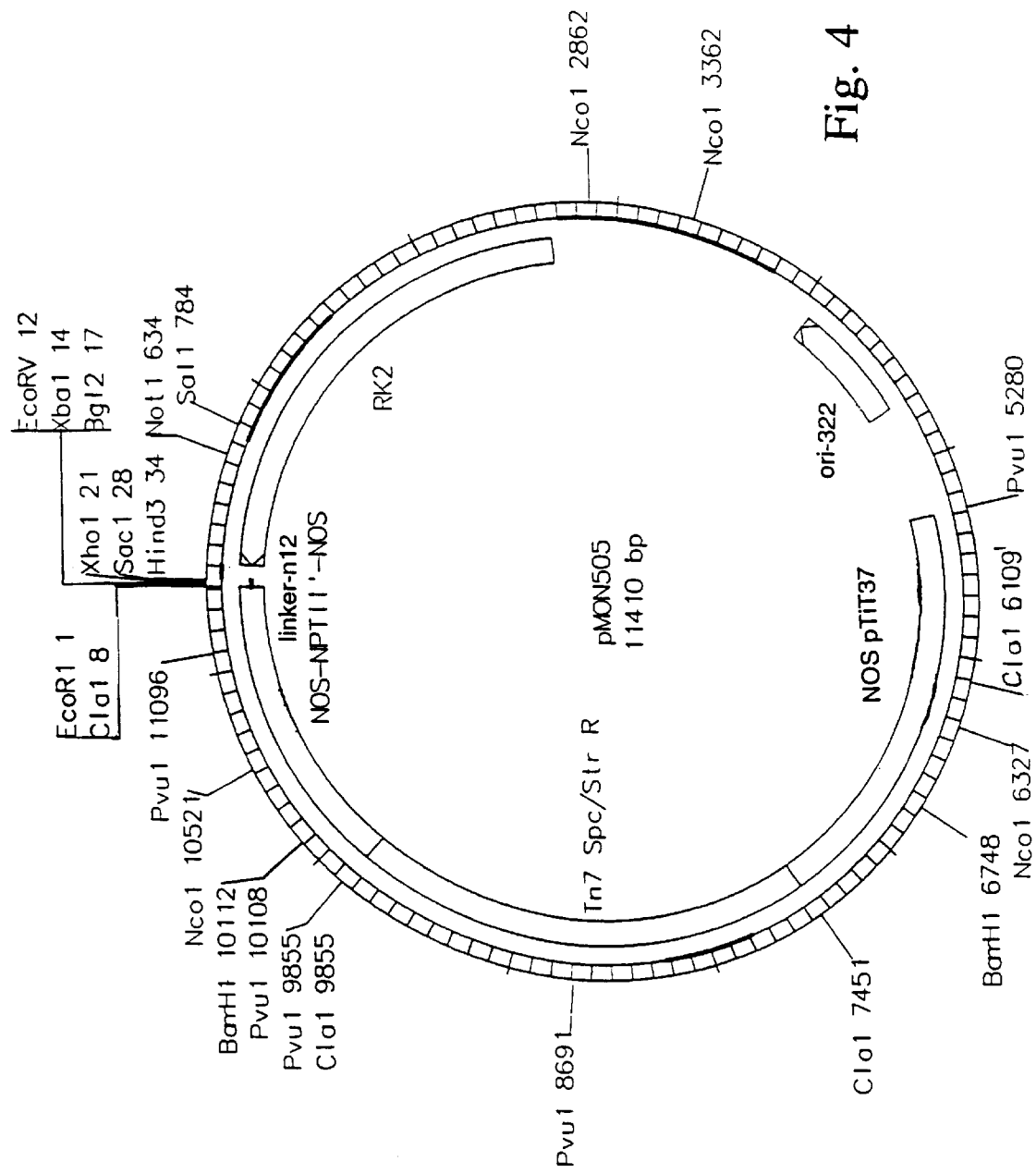
FIG. 4 represents a map of plasmid pMON505.

Referring to FIG. 4, plasmid pMON505 retains all the important features of pMON200 including the synthetic multi-linker for insertion of desired DNA fragments, the chimeric NOS-NPTII'-NOS kanamycin resistance determinant for selection in transgenic plants and a streptomycin/spectinomycin gene for selection in *E. coli* and *A. tumefaciens*, an intact nopaline synthase gene for facile scoring of transformants and inheritance in progeny and a pBR322 origin of replication for ease in making large amounts of the vector in *E. coli*. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Plasmid pMON546 contained (1) the CaMV35S/EPSP synthase gene; (2) a selectable marker gene for kanamycin resistance (Kan); (3) a nopaline synthase (NOS) gene as a scorable marker; and (4) a right T-DNA border, which effectively caused the entire plasmid to be treated as a "transfer DNA" (T-DNA) region by *A. tumefaciens cells.*

This plasmid was inserted into *A. tumefaciens* cells which contained a helper plasmid, pGV3111-SE. The helper plasmid encodes certain enzymes which are necessary to cause DNA from pMON546 to be inserted into plant cell chromosomes. It also contains a gene which confers resistance to the antibiotic kanamycin in bacteria.

A culture of *A. tumefaciens* containing pMON546 and pGV3111-SE was deposited with the American Type Culture Collection (ATCC) and was assigned ATCC accession number 53213. If desired, either one of these plasmids may be isolated from this culture of cells using standard methodology. For example, these cells may be cultured with *E. coli* cells which contain a mobilization plasmid, such as pRK2013 (Ditta 1980). Cells which become Spc/Str$^R$, Kan$^S$ will contain pMON546, while cells which become Kan$^R$, Spc/Str$^s$ will contain pGV3111-SE.

The above description for obtaining plant transformation vectors containing an EPSPS cDNA can be applied to other plant species and the illustration of its application in petunia is only exemplary. One of ordinary skill in the art could perform the same procedures or make the necessary modifications to the procedures to suit a particular plant species of interest. Such methods and modifications are known to those of ordinary skill in the art. The cDNA clones so isolated would then be suitable for introducing the mutations described in the present invention into the EPSPS gene by known methods.

GLYPHOSATE-TOLERANT PETUNIA PLANTS

Leaf disks with diameters of 6 mm (¼ inch) were taken from surface-sterilized petunia leaves. They were cultured on MS104 agar medium for 2 days to promote partial cell wall formation at the wound surfaces. They were then submerged in a culture of *A. tumefaciens* cells containing both pMON546 and GV3111-SE which had grown overnight in Luria broth at 28° C., and shaken gently. The leaf disks were removed from the bacterial suspension, blotted dry, and incubated upside down on filter paper placed over "nurse" cultures of tobacco cells, as described by Horsch (1980). After 2 or 3 days, the disks were transferred to petri dishes containing MS media with 500 µg/ml carbenicillin and 0. 0.1, 0.25, or 0.5 mM glyphosate (sodium salt), with no nurse cultures.

Control tissue was created using *A. tumefaciens* cells containing the helper plasmid pGV3111-SE and a different plant transformation vector, pMON505, which contained a T-DNA region with a NOS/NPTII/NOS kanamycin resistance gene and a NOS selectable marker gene identical to pMON546, but without the CaMV35S/EPSP synthase gene.

Within 10 days after transfer to the media containing glyphosate, actively growing callus tissue appeared on the periphery of all disks on the control plate containing no glyphosate. On media containing 0.1 mM glyphosate, there was little detectable difference between the control disks and the transformed tissue. At 0.25 mM glyphosate, there was very little growth of callus from control disks, while substantial growth of transformed tissue occurred. At 0.5 mM glyphosate, there was no callus growth from the control disks, while a significant number of calli grew from the transformed disks. This confirms that the CaMV35S/EPSP synthase gene conferred glyphosate resistance upon the transformed cells.

Transformed petunia plants were produced by regeneration from the above-described transformed leaf disks by the procedure described by Horsch, et al. (1985). The transformed plants obtained contained the pMON546 vector, described hereinabove, which contains the CaMV35S promoter fused to the wild-type petunia EPSP synthase gene.

Four individual representative transgenic seedlings were selected, grown and tested in the testing procedure described below, along with four individual non-transformed (wild-type) petunia seedlings.

The plants were grown in a growth medium in a growth chamber at 26° C. with 12 hours of light per day. The plants were fertilized weekly with a soluble fertilizer and watered as needed. The plants were sprayed at a uniform and reproducible delivery rate of herbicide by use of an automated track sprayer. The glyphosate solution used was measured as pounds of glyphosate acid equivalents per acre, mixed as the glyphosate isopropylamine salt, with an ionic surfactant.

Four individual wild-type (non-transformed) petunia plants were selected for use as control plants. Four individual transformed plants containing the pMON546 vector were selected by kanamycin resistance as described by Horsch, et al. (1985).

The control plants and the transformed plants were sprayed with the isopropylamine salt of glyphosate at the application level listed in Table 2 below; the experimental results obtained are also summarized in Table 2.

TABLE 2

| Plant Response to Glyphosate Spraying | | |
|---|---|---|
| Plant Type | Glyphosate Dose* | Visual Appearance |
| Control[1] | 0.8 #/acre | completely dead, plants showed very rapid chlorosis and bleaching, wilted and died |
| Chimeric ESPS | 0.8 #/acre | growing well, showed slight chlorosis in new leaves which are growing with normal morphology, plants appear healthy and started to flower |

*Acid Equivalent (0.8 #/acre = 0.897 kg/hectare)
[1]wild-type plant or transformed with control vector (pMON505)

As indicated in Table 2, the control plants were killed when sprayed with 0.8 pounds/acre of glyphosate. In contrast, the petunia plants which were transformed were healthy and viable after spraying with 0.8 pounds/acre. The transformed plants are more resistant to glyphosate exposure than the nontransformed control plants. Glyphosate tolerance was achieved in these transgenic tobacco plants by overexpressing the wild type petunia EPSP synthase cDNA from the high level expressing CaMV35S promoter. In order to achieve higher levels of tolerance, so that transgenic plants would be tolerant to glyphosate at typical use rates, glyphosate tolerant EPSP synthase variants were utilized. The following are examples where the glyphosate tolerant EPSP containing the glycine 101 to alanine substitution and EPSP variants containing the glycine 101 to alanine and alanine 192 to threonine variants are incorporated into plant transformation vectors and used to produce glyphosate tolerant transgenic plants.

Glyphosate-Tolerant Petunia EPSP Synthase

A plant transformation vector carrying a glycine (101) to alanine petunia EPSP synthase variant was prepared in the following manner.

Plasmid pMON530 DNA was digested with BglII and ClaI, to which was added the 330 bp BglII-EcoRI EPSP synthase 5' fragment from pMON536 and purified 1.4 kb EcoRI-ClaI EPSP synthase 3' fragment from pMON9566 and then treated with T4 DNA ligase. Following transformation a plasmid was isolated that carried the intact glycine (101) to alanine variant EPSP synthase coding sequence of petunia (with the coding sequence for the chloroplast transit peptide) adjacent to the CaMV35S promoter. This plasmid was designated pMON567. Plasmid pMON567 was inserted into *A. tumefaciens* cells that contained helper plasmid pGV3111-SE.

A culture of *A. tumefaciens* cells containing pMON567/pGV3111-SE was co-cultured with leaf disks taken from tobacco plants (*Nicotiana tobacam* CV H425) as described by Horsch (1985). The *Agrobacterium* cells inserted the variant EPSP synthase gene into the chromosomes of the plant cells. Plant cells resistant to kanamycin were selected and regenerated into differentiated plants by the procedure of Horsch (1985).

Progeny of these plants were propagated and grown to a rosette diameter of about 10 cm corresponding to a plant age of about four weeks. The plants were sprayed with glyphosate at levels corresponding to 0.4, 2.0 and 3.6 pounds acid equivalent/acre. The effect of glyphosate on the transformed plants were scored at 7, 14 and 28 days. The effect was translated to a numerical scale of 0–10 in which 0 represents total kill and 10 is the normal, unsprayed plant. The data below demonstrates that tobacco plants transformed with the glyphosate-tolerant EPSP synthase gene of petunia exhibit substantial tolerance even to these high levels of glyphosate. The values represent the best transformant for both wild-type EPSP synthase and glyphosate-tolerant EPSP synthase genes.

TABLE 3

Relative Effect of Glyphosate[1]

| | Pounds/Acre (kg/hectare) | | | | | |
|---|---|---|---|---|---|---|
| | 0.4 (0.448) | | 2.0 (2.242) | | 3.6 (4.035) | |
| Day | GT[2] | WT[3] | GT | WT | GT | WT |
| 7 | 8.0 | 6.0 | 8.0 | 5.0 | 5.0 | 5.0 |
| 14 | 8.0 | 7.0 | 8.3 | 1.8 | 7.4 | 1.7 |
| 28 | 9.0 | 9.0 | 7.0 | 0.8 | 7.0 | 0.8 |

[1]0 represents total kill and 10 represents no effect.
[2]Glyphosate-tolerant petunia EPSP synthase.
[3]Wild-type EPSP synthase.

II. EPSP SYNTHASE GENOMIC CLONE OF ARABIDOPSIS

An *Arabidopsis thaliana* genomic bank was prepared by cloning size fractionated (15–20 kb) MboI partially digested DNA into BamHI and EcoRI digested lambda EMBL3 (Stratagene Cloning Systems, San Diego, Calif.). Approximately 10,000 plaques of phage from this library were screened with $^{32}$P labeled petunia EPSP synthase probe (pMON9566 described hereinbefore). A strongly hybridizing plaque, designated E1, was purified. Southern blots of the phage DNA with the EPSP synthase probe identified two fragments which hybridized very strongly. The first fragment was a 1.0 kb HindIII fragment and the other was a 700 bp BamHI fragment. These fragments were cloned into plasmid pUC119 and designated pMON574 and pMON578.

The DNA sequences for the two inserts were then determined by the method of Sanger (1977). The sequence data indicated that the phage did contain the EPSP synthase gene of Arabidopsis by its strong homology to the petunia EPSP synthase sequence. The 700 bp BamHI fragment was used as a hybridization probe against the phage and Arabidopsis genomic DNA to identify restriction fragments suitable for the cloning of the entire EPSP synthase gene. Two hybridizing BglII fragments of 6.0 kb and 3.1 kb were identified in the E1 phage clone. These fragments were separately subcloned into pMON550 to provide DNA for further experiments and designated pMON582 and pMON583, respectively. Plasmid pMON550 is a derivative of pUC19 (Yanisch-Perron et al 1985) produced by inserting the synthetic DNA fragment

5'-AGCTTTCTAGAAGATCTCCATGGAGGCCTGG-TAC-3

3'-AAGATCTTCTAGAGGTACCTCCGGAC-5'
into pUC19 digested with HindIII and KpnI. Two additional subclones were made from clones pMON582 and pMON583. Plasmid pMON584 is the 1.8 kb EcoRI to BamHI fragment containing the 5'-end of the Arabidopsis EPSP synthase gene in pUC118 which is prepared from pUC18 in a manner analogous to the preparation of pUC119 from pUC19 described hereinbefore. Plasmid pMON589 is the 2.8 kb BamHI to BglII fragment containing the 3'-end of the Arabidopsis EPSP synthase gene in pUC119. Sequence determination from the BamHI site of pMON584, and from the BamHI site of pMON589 completed the sequence of the coding regions of the gene.

Figure 5:
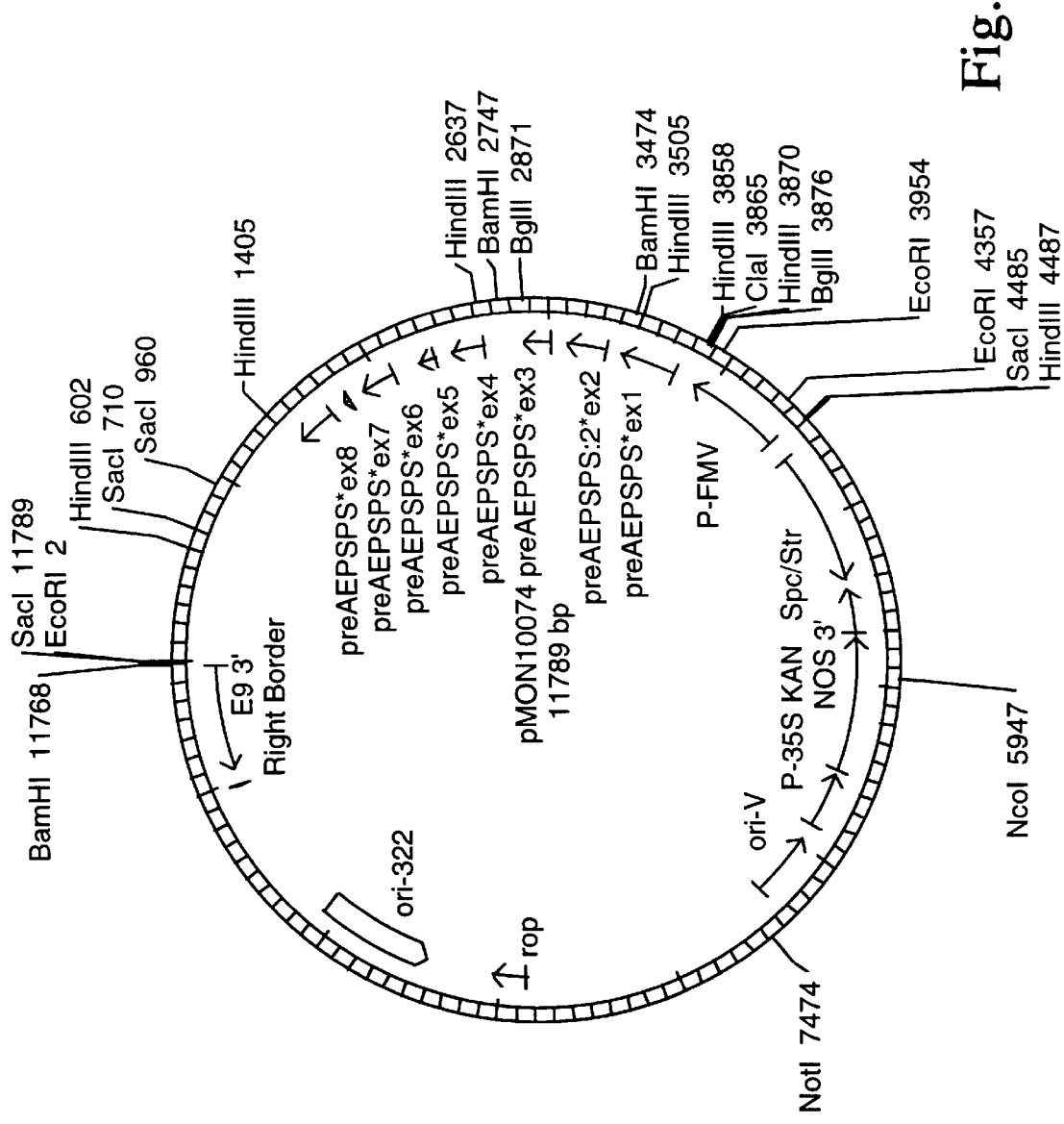
FIG. 5 represents a map of plasmid pMON10074.

The coding sequence was altered so that the Arabidopsis EPSP synthase would include the alanine for glycine substitution at position 101 of the mature enzyme. Plasmid pMON578 was mutagenized with the oligonucleotide:

5'-CTTTACCTCGGTAATGCAGCTACAGCAAT-GCG-3'
by the method of Kunkel (1985). A portion of the resulting plasmid, pMON594, was sequenced to verify the mutation. The alanine 192 to threonine amino acid change was introduced in the Arabidopsis EPSPS gene by site directed mutagenesis using the method of Kunkel and plasmid pMON10011. Plasmid pMON10011 contains a chimeric Arabidopsis EPSPS gene with the gly 101 to ala change fused to the enhanced 35S promoter and nopaline synthase 3' on a NotI restriction fragment in a pUC based phagemid vector. The vector also contains both pUC and M13 phage origins of replication along with an ampicillin resistance marker for selection in *E. coli*. Single strand DNA template was prepared from pMON10011 and mutagenized with the following oligonucleotide primer:

5'-ATGTCTGCTCCCTTAACCCTTGGAGACGTC-3'
The resulting plasmid, pMON8324, was partially sequenced to confirm the mutagenesis. The Arabidopsis gene containing both the glycine 101 to alanine and alanine 192 to threonine amino acid changes was assembled into pMON10074 for plant transformation experiments to produce glyphosate tolerant plants. The pMON10074 plasmid contains the following DNA segments (FIG. 5, clockwise). First, the 0.93 kb fragment isolated from transposon Tn7 which encodes bacterial spectinomycin/streptomycin resistance (Spc/Str), and is a determinant for selection in *E. coli* and *Agrobacterium tumefaciens* (Fling et al. 1985). This is joined to the chimeric kanamycin resistance gene engineered for plant expression to allow selection of the transformed tissue. The chimeric gene consists of the 0.35 kb cauliflower mosaic virus 35S promoter (P-35S) (Odell et al. (1985), the 0.83 kb neomycin phosphotransferase typeII gene (KAN), and the 0.26 Kb 3'-nontranslated region of the nopaline synthase gene (NOS 3') (Fraley et al. 1983). The next segment is the 0.75 kb origin of replication from the RK2 plasmid (ori-V) (Stalker et al. 1981). It is joined to the 3.1 kb SalI to PvuI segment of pBR322 which provides the origin of replication for maintenance in *E. coli* (ori-322), and the bom site for the conjugational transfer into the *Agrobacterium tumefaciens* cells. Next is the 0.36 kb PvuI to BclI fragment from the pTiT37 plasmid, which contains the nopaline-type T-DNA right border region (Fraley et al. 1985). The last segment is the chimeric gene engineered to overproduce the 5-enolpyruvylshikimate-3-phosphate synthase enzyme (EPSPS) in plants (Shah et al. 1986 and Klee et al. 1987). The chimeric gene consists of the 0.6 kb 35S promoter from the figwort mosaic virus (P-FMV) (Gowda et al. 1989), the 3.9 kb *Arabidopsis thaliana* EPSPS with two amino acid changes (gly-ala(101), ala-thr(192)), and the 0.7 kb 3' nontranslated region of the pea rbcS-E9 gene (E9 3') (Coruzzi et al 1984, and Morelli et al. 1985).

The pMON10074 vector was mobilized into the ABI Agrobacterium strain. The ABI strain is the A208 *Agrobacterium tumefaciens* carrying the disarmed Ti plasmid pTiC58 (Koncz and Schell 1986). The Ti plasmid does not carry the T-DNA phytohormone genes, and the strain is therefore unable to cause the crown gall disease. Mating of pMON10074 into ABI was done by the triparental conjugation system using the helper plasmid pRK2013 (Ditta et al. 1980). When the plant tissue is incubated with the ABI::pMON10074 conjugate, the vector is transferred to the plant cells by the vir functions encoded by the disarmed pTiC58 plasmid. The vector opens at the T-DNA right border region, and the entire pMON10074 vector sequence is inserted into the host plant chromosome. The pTiC58 Ti plasmid does not transfer to the plant cells but remains in the Agrobacterium.

A total of 15 transgenic canola plants containing the pMON10074 construct, and 2 non-transformed controls were sprayed with glyphosate at a commercial rate of 0.56 kg/ha. The effect of glyphosate on both the vegetative and reproductive performance of the sprayed plants was scored at 7, 14 and 28 days after spray. The effect of glyphosate was translated to a numerical scale of 0–10, where 0 represents total kill and 10 represents the normal, unsprayed plant. The non-transformed controls had vegetative scores of 2 after 14 days and reproductive scores of 0 after 28 days. The pMON10074 canola plants outperformed the controls with 6 out of 15 plants having vegetative scores greater than 8, with 1 scoring a 10, and 7 out of 15 had reproductive scores greater than 8 with 3 of them scoring 10. The data demonstrates that transformed canola plants containing the glyphosate tolerant glycine 101 to alanine, alanine 192 to threonine double variant EPSPS synthase are very tolerant to commercial applications of glyphosate, producing normal, fertile plants.

III. EPSP SYNTHASE GENE FROM MAIZE
Construction of a Glyphosate Tolerant Maize Gene Maize seeds were imbibed for 12 hours in water, the embryos, including the scutella, were dissected from the seeds and RNA was purified from this material by the method of Rochester et al. (1986). PolyA-mRNA was isolated from the RNA by chromatography on oligo dT cellulose, and was used to construct a cDNA library as hereinbefore described. (Gasser et al. 1989) The library was screened with a $^{32}$-P labelled RNA probe synthesized in vitro from pMON9717 (Gasser et al. 1988) which had been linearized with HindIII. The probe was synthesized with T7 RNA polymerase (Promega, Madison, Wis.) according to the manufacturers instructions. Hybridizing plaques were isolated, replated and nitrocellulose lifts from the plates were screened with the same probe. Plaques representing single clones which hybridized strongly to the tomato probe were isolated, propagated and used to prepare DNA. A clone designated lambda-zld was found to contain a 1.8 kb EcoRI insert. The insert of this phage was subcloned into the EcoRI site of Bluescript KS+ (Stratagene, San Diego, Calif.) to form pMON9935. The complete sequence of this cDNA clone was determined and used to deduce the amino acid sequence shown in FIG. 1. To facilitate future constructions an Xba I site was engineered immediately upstream of the first ATG initiation codon of this clone by oligonucleotide mediated mutagenesis by the method of Kunkel using the oligonucleotide:

5'-TACCAACCATCGGCGTCTAGAGGCAATGGC-GGC-3' producing plasmid pMON9950. pMON9950 was digested with Xba I and religated to eliminate the 126 bp Xba I fragment at the 5' end of the cDNA forming pMON9951. To produce a coding sequence which encodes for a glyphosate tolerant form of maize EPSP synthase, pMON9951 was mutated by the method of Kunkel using the oligonucleotide:

5'-CTTCTTGGGGAATGCTGCTACTGCAATGCG-GC-3' resulting in pMON9960. This mutagensis will change a GGA codon to a GCT codon, changing the second glycine residue in the conserved sequence -L-G-N-A-G-T-A- to an alanine in the resulting protein. The glycine residue is amino acid 163 of the predicted maize preEPSP synthase. This would correspond to a position between amino acid 95–105 of the mature protein depending on the precise transit peptidase cleavage site which has not been determined. pMON9960 was then mutagenized by the same method with the oligonucleotide:

5'-GATGGCTGCTCCTTTGACTCTTGGGGATG-3 resulting in the formation of a maize EPSP synthase which would include the alanine for threonine substitution at position 254 of the maize EPSP synthase precursor. This would correspond to a position between amino acid residues 187 and 197 of the mature protein.

For expression in maize cells the coding sequence of the glyphosate tolerant variant form of maize pre-EPSP synthase is inserted between a promoter known to function in maize cells, such as the CaMV35S promoter, and the poly A addition site of the nopaline synthase gene or another suitable gene. In addition, an intron such as the first intron of the maize ADH1 gene may be included in the 5'-untranslated region of the expression unit which may enhance expression of the chimeric gene (Callis et al., 1987).

Transgenic maize cells can be prepared by bombarding maize cells, such as the suspension line BMSl (ATCC 54022), with particles coated with plasmid DNA by the method of Klein et al. (1988) or the method of Fromm et al. (1990). The cells are then selected for 1–3 weeks in medium containing 5 mM glyphosate followed by selection on solid medium containing 5 mM glyphosate. Calli which have incorporated and are expressing the chimeric variant EPSP synthase gene can be identified by their rapid growth on the solid medium.

Alternatively the EPSP synthase expression unit is inserted into a vector which includes the neomycin phosphotransferase gene under control of the CaMV35S promoter, or a similar vector with a different marker gene that allow for a selection of transformed maize cells. This vector, or a similar vector using any other glyphosate resistant coding sequences constructed as described in the claims and examples of this application, is then introduced into maize cells as described in the following example.

Preparation of Maize Protoplasts

Protoplasts are prepared from a Black Mexican Sweet (BMS) maize suspension line, BMSI (ATCC 54022) as described by Fromm et al. (1985 and 1986). BMSI suspension cells are grown in BMS medium which contains MS salts, 20 g/l sucrose, 2 mg/l 2,4 dichlorophenoxy acetic acid, 200 mg/l inositol, 130 mg/l asparagine, 1.3 mg/l niacin, 0.25 mg/l thiamine, 0.25 mg/l pyridoxine, 0.25 mg/l calcium pantothenate, pH 5.8. 40 ml cultures in 125 erlenmeyer flasks are shaken at 150 rpm at 26° C. The culture is diluted with an equal volume of fresh medium every 3 days. Protoplasts are isolated from actively growing cells 1 to 2 days after adding fresh medium. For protoplast isolation, cells are pelleted at 200×g in a swinging bucket table top centrifuge. The supernatant is saved as conditioned medium for culturing the protoplasts. Six ml of packed cells are resuspended in 40 ml of 0.2M mannitol/50 mM $CaCl_2$/10 mM sodium acetate which contains 1% cellulase, 0.5% hemicellulase and 0.02% pectinase. After incubation for 2 hours at 26° C., protoplasts are separated by filtration through a 60 μm nylon mesh screen, centrifuged at 200×g and washed once in the same solution without enzymes.

Transformation of Maize Protoplasts Using an Electroporation Technique

Protoplasts are prepared for electroporation by washing in a solution containing 2 mM potassium phosphate pH 7.1, 4 mM calcium chloride, 140 mM sodium chloride and 0.2M mannitol. After washing, the protoplasts are resuspended in the same solution at a concentration of 4×10$^6$ protoplasts per ml. One-half ml of the protoplast containing solution is mixed with 0.5 ml of the same solution containing 50 micrograms of supercoiled plasmid vector DNA and placed in a 1 ml electroporation cuvette. Electroporation is carried out as described by Fromm et al. (1986). As described, an electrical pulse is delivered from a 122 or 245 microFarad capacitor charged to 200 V. After 10 minutes at 4° C. and 10 minutes at room temperature protoplasts are diluted with 8 ml of medium containing MS salts 0.3M mannitol, 2% sucrose, 2 mg/l 2,4-D, 20% conditioned BMS medium (see above) and 0.1% low melting agarose. After 2 weeks in the dark at 26° C., medium without mannitol and containing kanamycin is added to give a final concentration of 100 mg/l kanamycin. After an additional 2 weeks, microcalli are removed from the liquid and placed on a membrane filter disk above agarose-solidified medium containing 100 mg/l kanamycin. Kanamycin resistant calli composed of transformed maize cells appear after 1–2 weeks.

Glyphosate tolerant maize cells

As described by Fromm et al. (1986), transformed maize cells can be selected by growth in kanamycin containing medium following electro-poration with DNA vectors containing chimeric kanamycin resistance genes composed of the CaMV35S promoter, the NPTII coding region and the NOS 3' end. These cells would also be producing the glyphosate tolerant form of EPSP synthase and would tolerate elevated levels of glyphosate.

The electroporated cells could also be selected as described above by transferring them directly into glyphosate containing liquid medium followed by selection on solid medium containing glyphosate.

Alternative methods for the introduction of the plasmids into maize, or other monocot cells would include, but are not limited to, the injection method of Newhaus et al. (1987), the injection method of de la Pena et al. (1987) or the microprojectile methods of Klein et al. (1987) and McCabe et al. (1988).

IV. INTRODUCTION OF A GENE ENCODING GLYPHOSATE TOLERANT EPSPS INTO OTHER PLANT SPECIES

A gene encoding the variant EPSPS enzyme of the present invention having a glycine to alanine substitution at position 101 and an alanine to threonine substitution at position 192 of the mature EPSPS enzyme has also been introduced into other plant species such as tobacco, sugarbeet, tomato, soybean and cotton. The plants transformed with a vector containing the variant DNA encoding the EPSPS enzyme of the present invention have also exhibited glyphosate tolerance. In particular, the glycine to alanine and alanine to threonine substitutions of the present invention have been introduced into a genomic clone of the Arabidopsis EPSPS gene and this gene introduced into canola and tobacco plants using suitable plant transformation vectors. The resulting transformed plants exhibited tolerance to glyphosate.

From the foregoing, it will be seen that this invention is one well adapted to attain all the ends and objects hereinabove set forth together with advantages which are obvious and which are inherent to the invention.

The embodiments described above are provided to better elucidate the practice of the present invention. Since many possible embodiments may be made of the invention without departing from the scope thereof, it should be understood that these embodiments are provided for illustrative purposes only, and are not intended to limit the scope of the invention.

It will be understood that certain features and subcombinations are of utility and may be employed without reference to other features and subcombinations. This is contemplated by and is within the scope of the claims.

BIBLIOGRAPHY

Adams, S. P. and Galluppi, G. R. (1986) *Medicinal Research Reviews* 6:135–170.
Adams, S. P., et al., (1983) *J. Amer. Chem. Soc.* 105:661.
Ausubel, F., et al., (1980) *Plant Mol. Bio. Newsletter*
Bachman, B. J., et al., (1980) *Microb. Rev.* 44:1–56.
Brau, et al., *Mol. Gen. Genet.* 193:179–187 (1984).
Broglie, R., et al., (1983) *Bio/Technology* 1:55–61.
Broglie, R., et al., (1984) *Science* 224:838–843.
Callis, J., Fromm, M. and Walbot, V. (1987) *Genes and Develop.* 1:1183–1200.
Charles, G., Keyte, J. W., Brammer, W. J., Smith, M. and Hawkins, A. R. (1986) *Nucleic Acids Res.* 14:2201–2213.
Coruzzi, G., Broglie, R., Edwards, C., and Chua, N. H. (1984). *EMBO J* 3, 1671–1679.
Covey, S., Lomonosoff, G. and Hill, R., (1981) *Nucleic Acids Res.* 9:6735.
de la Pena, A., Lorz, H. and Schell, J. (1987) *Nature* 325:274–276.
DePicker, A., et al., (1982) *J. Mol. Appl. Gen.* 1:561.
Ditta, G., et al., (1980) *Pro. Natl. Acad. Sci. USA* 77:7347–7351.
Duncan, K., Lewendon, A. and Coggins, J. R. (1984) *FEBS Lett.* 170:59–63.
Fling, M. E., Kopf, J., and Richards, C. (1985). *Nucleic Acids Research* 13 no.19, 7095–7106.
Fraley, R. T., Rogers, S. G., Horsch, R. B., Sanders, P. R., Flick, J. S., Adams,S. P., Bittner, M. L., Brand, L. A., Fink, C. L., Fry, J. S., Galluppi, G. R., Goldberg, S. B., Hoffmann, N. L., and Woo, S. C. (1983). *Proc Natl Acad Sci USA* 80, 4803–4807.
Fraley, R. T., Rogers, S. G., Horsch, R. B., Eichholtz, D. A., Flick, J. S., Fink, C. L., Hoffmann, N. L. and Sanders, P. R. (1985) *Bio/Technology* 3:629–635.
Fromm, M., Taylor, L. P. and Walbot, V. (1985) *Proc. Nat. Acad. Sci. USA* 82:5824–5828.
Fromm, M., Taylor, L. P. and Walbot, V. (1986) *Nature* 319:791–793.
Fromm, M. E., F. Morrish, C. Armstrong, R. Williams, J. Thomas, T. Klein (1990) *Bio/Technology* 8:833–839.
Gardner, R., Howarth, A., Hahn, P., Brown-Luedi, M., Shepherd, R. and Messing, J., (1981) *Nucleic Acids Res.* 9:2871.
Gasser et al., (1988) *J. Biol. Chem.* 9:4280–4287.
Gasser et al. (1989) *Plant Cell* 1:15–24.
Goldberg, R. B. et al., (1981) *Devel. Bio.* 83:201–217.
Gowda, S., Wu, F. C., and Shepard, R. J. (1989). Journal of Cellular Biochemistry supplement 13D, 301.(Abstract)
Gritz and Davies, *Gene* 25:179–188.
Gubler, U., and Hoffman, B. H. (1983) *Gene* 25:263–269.
Guilley, H., Dudley, R., Jonard, G., Balax, E. and Richards, K. (1982) *Cell* 30:763.
Horii, T. et al. (1980) *P.N.A.S. USA* 77:313.
Horsch, R. and Klee, H., (1986) *Proc. Natl. Acad. Sci. USA* vol.83, 442–4432.
Hunkapiller, M. W., et al. (1983b) *Methods Enzymol.* 91:486–493. Huynh, T. B., Young, R. A., and Davis, R. W. (1985) *DNA Cloning Techniques: A Practical Approach*, D. Glover, ed., IRL Press, Oxford.
Kay, R., Chan, A., Daly, M., and McPherson, J. (1987) *Science* 236:1299–1302.
Klee, H. J., Muskopf, Y. M., and Gasser, C. S. ( 1987). *Mol Gen Genet* 210,437–442.
Klein, T. M., Wold, E. D., Wu, R. and Sanford, J. C. (1987) *Nature* 327:70–73.

Koncz, C., and Schell, J. (1986). *Mol Gen Genet* 204, 383–396.

Krieg, P. A. and Melton, D. A. (1984) *Nucleic Acids Res.* 12:7057–7070.

Kunkel (1985) *P.N.A.S. USA* 82:488–492.

Lemke, G. and Axel, R. (1985) *Cell* 40:501–508.

Maniatis, T., et al. (1982) *Molecular Cloning: A Laboratory Manual*, Cold Spring Harbor Labs., NY.

Marmur, J. (1961) *J. Mol. Biol.* 3:208–210.

Maskell, D. J. et al. (1988) *J. Bacteriology* 170, 6:2467–2471.

Maxam, A. M. and Gilbert, W., (1977) *P.N.A.S. USA* 74:560–564.

McCabe, D. E., et al. (1988) *Bio/Technology* 6:923.

Messing, J. et al. (1981) *Nucleic Res.* 9:309–321.

Morelli, G., Nagy, F., Fraley, R. T., Rogers, S. G., and Chua, N. H. (1985). *Nature* 315, 200–204.

Mousdale, D. M. and Coggins, J. R. (1984) *Planta* 164:78–83.

Neuhaus, G. et al. (1987) *Theor. Appl. Genet.* 75:30.

Odell, J. T., Nagy, F., and Chua, N. H. (1985). *Nature* 313, 810–812.

Okayama, H. and Berg, P. (1982) *Mol. Cell. Biol.* 2:161.

Padgette, S. R., et al. (1987) *Arch. Biochem. Biophys.* 258:564–573.

Rao, R. N. and Rogers, S. G. (1979) *Gene* pp. 7:79–82.

Rochester, D. E., Winter, J. A. and Shah, D. M. (1986) *EMBO J.* 5:452–458.

Rogers, S., Horsch, R. and Fraley, R. (1986) *Methods in Enzymology* Vol. 118 (H. Weissbach and A. Weissbach, eds.) p.627, Academic Press, New York.

Rogers, S. G., et al. (1983) *Appl. Envir. Microbio.* 46:37–43.

Rogers, S., Klee, :H., Horsch, R. and Fraley, R. (1987) *Methods in Enzymology* Vol. 153 (R. Wu and L. Grossman, eds.) p.253, Academic Press, New York.

Sancar, A., et al. (1980) *P.N.A.S. USA* 77:2611.

Sanger, et al. (1977) *Proc. Natl. Acad. Sci. USA* 74:5463.

Scherer, et al. (1981) *Developmental Bio* 86:438–447.

Schimke, R. T. ed. (1982) *Gene Amplification*, Cold Spring Harbor Labs.

Schmidhauser, T. and Helinski, D. (1985) *J. Bacteriology* 164:446.

Schuler, M. A., Schmitt, E. S. and Beachy, R. N. (1982) *Nucl Acids Res.* 10:8225–8244.

Shah, D., Horsch, R., Klee, H., Kishore, G., Winter, J., Tunmer, N., Hironaka, C., Sanders, P., Gasser, C., Aykent, S., Siegal, N., Rogers, S., and Fraley, R. (1986). *Science* 233,478–481.

Soberson, et al. (1980), *Gene* 9:287–305.

Southern, E. M. (1975) *J. Mol. Biol.* 98:503–517.

Stalker, D. M., Thomas, C. M., and Helinski, D. R. (1981). *Mol Gen Genet* 181, 8–12.

Stalker, D. M., Hiatt, W. R. and Comai, L. (1985) *J. Biol. Chem.* 260:4724–4728.

Steinrucken, H. and Amrhein, N. (1980) *Biochem. & Biophys. Res. Comm.* 94:1207–1212.

Vieira, J. et al. (1982) *Gene* 19:259–268.

Yanisch-Perron, C., Vieira, J. and Messing, J. (1985) *Gene* 33:103–119.

Zoller, M. M. et al. (1983) *Methods Enzymol.* 100:468.

We claim:

1. A method for producing a gene encoding a glyphosate-tolerant 5-enolpyruvyl-3-phosphoshikimate (EPSP) synthase enzyme which comprises substituting, in a EPSP synthase gene encoding a protein containing the amino acid sequences shown below located in the indicated positions, a codon encoding an alanine residue for the second glycine residue in a first amino acid sequence:

-L-G-N-A-G-T-A- located between positions 80 and 120 in the mature EPSP synthase enzyme, and further substituting a codon encoding a threonine residue for the codon encoding the terminal alanine residue in a second amino acid sequence:

-A-L-L-M-$X_1$-A-P-L-A- where $X_1$ is either alanine, serine or threonine, and where said second amino acid sequence is located between positions 170 and 210 in the mature EPSP synthase enzyme.

2. A method of claim 1 in which the glyphosate-tolerant EPSP synthase gene is produced from a plant EPSP synthase gene.

3. A method of claim 1 in which the glyphosate-tolerant EPSP synthase gene is produced from a bacterial EPSP synthase gene.

4. The method for producing a gene of claim 1 which comprises making the indicated codon substitutions in a EPSP synthase gene encoding a protein of FIG. 1.

5. A gene encoding a glyphosate-tolerant 5-enolpyruvyl-3-phosphoshikimate (EPSP) synthase enzyme which encodes a first amino acid sequence:

-L-G-N-A-A-T-A- between positions 80 and 120 in the mature EPSP synthase enzyme, and encodes a second amino acid sequence:

-A-L-L-M-$X_1$-A-P-L-T- where $X_1$ is either alanine, serine or threonine, where said second amino acid sequence is located between positions 170 and 210 in the mature EPSP synthase enzyme.

6. The gene of claim 5 encoding a protein as shown in FIG. 1 but which protein contains the first and second amino acid sequences.

7. A gene encoding a glyphosate-tolerant EPSP synthase produced by the method of claim 1 wherein the EPSP synthase gene in which the codon substitutions are made is selected from the group of EPSP synthase consisting of petunia, tomato, maize, *Arabidopsis thaliana*, soybean, *Brassica napus, E. coli* K-12, and *Salmonella typhimurium* proteins as shown in FIG. 1.

8. A plant gene encoding a glyphosate-tolerant EPSP synthase enzyme of claim 5.

9. A plant transformation vector comprising a gene which encodes a glyphosate-tolerant 5-enolpyruvyl-3-phosphoshikimate (EPSP) synthase having a first amino acid sequence:

-L-G-N-A-A-T-A- located between positions 80 and 120 of the mature EPSP synthase sequence and a second amino acid sequence:

-A-L-L-M-$x_1$-A-P-L-T- where $x_1$ is either alanine, serine or threonine, where said second amino acid sequence is located between positions 170 and 210 in the mature EPSP synthase sequence.

10. A vector of claim 9 containing a glyphosate-tolerant plant EPSP synthase.

11. A vector of claim 9 containing a glyphosate-tolerant bacterial EPSP synthase.

12. A transformed plant cell containing a gene of claim 8.

13. A transformed plant cell of claim 12 selected from the group consisting of tomato, tobacco, oil seed rape, flax, soybean, sunflower, sugar beet, alfalfa, cotton, rice and maize.

14. A transformed cell of claim 12 from tomato.

15. A transformed cell of claim 12 from tobacco.

16. A transformed cell of claim 12 from oil seed rape.

17. A transformed cell of claim 12 from flax.

18. A transformed cell of claim 12 from soybean.

19. A transformed cell of claim 12 from sunflower.

20. A transformed cell of claim 12 from sugar beet.
21. A transformed cell of claim 12 from alfalfa.
22. A transformed cell of claim 12 from maize.
23. A dicot plant comprising transformed plant cells of claim 12.
24. A plant of claim 23 in which the plant is tomato.
25. A plant of claim 23 in which the plant is tobacco.
26. A plant of claim 23 in which the plant is oil seed rape.
27. A plant of claim 23 in which the plant is flax.
28. A plant of claim 23 in which the plant is sunflower.
29. A plant of claim 23 in which the plant is sugar beet.
30. A plant of claim 23 in which the plant is alfalfa.
31. A monocot plant comprising transformed plant cells of claim 12, wherein said monocot plant is selected from the group consisting of rice and maize.
32. A seed produced by the plant of claim 23.
33. A seed of claim 32 in which the plant is tomato.
34. A seed of claim 32 in which the plant is tobacco.
35. A seed of claim 32 in which the plant is oil seed rape.
36. A seed of claim 32 in which the plant is flax.
37. A seed of claim 32 in which the plant is sunflower.
38. A seed of claim 32 in which the plant is sugar beet.
39. A seed of claim 32 in which the plant is alfalfa.
40. A seed produced by the plant of claim 31.
41. A method for producing glyphosate-tolerant plants which comprises propagating dicot plants transformed with the gene of claim 5.
42. The method of claim 41 in which the propagated plant is selected from the group consisting of tomato, tobacco, oil seed rape, flax, sunflower, sugar beet, alfalfa and cotton.
43. A method for producing glyphosate-tolerant plants which comprises propagating monocot plants transformed with the gene of claim 5, wherein said monocot plants are selected from the group consisting of rice and maize.
44. The method of claim 41 wherein a first plant is propagated by crossing between said first plant and a second plant, such that at least some progeny of said cross display glyphosate tolerance.
45. The method of claim 44 wherein the plant is selected from the group consisting of tomato, tobacco, oil seed rape, flax, sunflower, sugar beet, alfalfa, and cotton.
46. The method of claim 43 wherein a first plant is propagated by crossing between said first plant and a second plant, such that at least some progeny of said cross display glyphosate tolerance.
47. A DNA sequence encoding a glyphosate-tolerant EPSP synthase, wherein said DNA sequence comprises the gene of claim 5 and is less than twenty kilobases in length.

48. The DNA sequence of claim 47 encoding a glyphosate-tolerant plant EPSP synthase.
49. The DNA sequence of claim 47 encoding a glyphosate-tolerant bacterial EPSP synthase.
50. A method for selectively controlling weeds in a field containing a dicot crop having planted dicot crop seeds or dicot plants comprising the steps of:

planting said dicot crop seeds or dicot plants which are glyphosate-tolerant as a result of being transformed with a gene encoding a glyphosate-tolerant EPSP synthase enzyme which contains the amino acid sequence -L-G-N-A-A-T-A- between positions 80 and 120 in the mature EPSP synthase sequence, and a second amino acid sequence -A-L-L-M-$X_1$-A-P-L-T-, wherein $X_1$ is either alanine, serine or threonine, and where said second amino acid sequence is located between positions 170 and 210 in the mature EPSP synthase sequence; and applying to said crop and weeds in said field a sufficient amount of glyphosate to control said weeds without significantly affecting said crop.

51. The method of claim 50 wherein said gene encoding a glyphosate-tolerant EPSP synthase enzyme is from a plant source.
52. A method for selectively controlling weeds in a field containing a maize or rice crop having planted maize or rice crop seeds or plants, comprising the steps of:

planting said maize or rice crop seeds or plants which are glyphosate-tolerant as a result of being transformed with a gene encoding a glyphosate-tolerant EPSP synthase enzyme which contains the amino acid sequence -L-G-N-A-A-T-A- between positions 80 and 120 in the mature EPSP synthase sequence, and a second amino acid sequence -A-L-L-M-$X_1$-A-P-L-T-, wherein $X_1$ is either alanine, serine or threonine, and where said second amino acid sequence is located between positions 170 and 210 in the mature EPSP synthase sequence; and applying to said crop and weeds in said field a sufficient amount of glyphosate to control said weeds without significantly affecting said crop.

53. The method of claim 52 wherein said gene encoding a glyphosate-tolerant EPSP synthase enzyme is from a plant source.

\* \* \* \* \*